US011149065B2

(12) United States Patent
Cai et al.

(10) Patent No.: US 11,149,065 B2
(45) Date of Patent: Oct. 19, 2021

(54) ONE-BEAD-TWO-COMPOUND MACROCYCLIC LIBRARY AND METHODS OF PREPARATION AND USE

(71) Applicant: University of South Florida, Tampa, FL (US)

(72) Inventors: Jianfeng Cai, Tampa, FL (US); Yan Shi, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/916,517

(22) Filed: Jun. 30, 2020

(65) Prior Publication Data
US 2020/0377552 A1 Dec. 3, 2020

Related U.S. Application Data

(62) Division of application No. 15/947,587, filed on Apr. 6, 2018, now Pat. No. 10,738,082.

(60) Provisional application No. 62/483,038, filed on Apr. 7, 2017.

(51) Int. Cl.
| | |
|---|---|
| C07K 7/54 | (2006.01) |
| A61K 38/12 | (2006.01) |
| A61P 35/00 | (2006.01) |
| C40B 40/10 | (2006.01) |
| C40B 50/16 | (2006.01) |
| C07K 1/04 | (2006.01) |
| A61K 38/00 | (2006.01) |
| C07K 7/06 | (2006.01) |
| C07K 17/14 | (2006.01) |
| G01N 33/566 | (2006.01) |
| C40B 30/04 | (2006.01) |

(52) U.S. Cl.
CPC ............. *C07K 7/54* (2013.01); *A61K 38/00* (2013.01); *A61K 38/12* (2013.01); *A61P 35/00* (2018.01); *C07K 1/04* (2013.01); *C07K 1/047* (2013.01); *C07K 7/06* (2013.01); *C07K 17/14* (2013.01); *C40B 40/10* (2013.01); *C40B 50/16* (2013.01); *G01N 33/566* (2013.01); *C40B 30/04* (2013.01)

(58) Field of Classification Search
CPC . C07K 7/54; C07K 1/04; C07K 1/047; C07K 7/06; C07K 17/14; A61P 35/00; A61K 38/00; A61K 38/12; C40B 40/10; C40B 50/16; C40B 30/04; G01N 33/566
See application file for complete search history.

(56) References Cited

U.S. PATENT DOCUMENTS 10,738,082 B2  8/2020 Cai et al.
2018/0291063 A1 10/2018 Jianfeng

OTHER PUBLICATIONS

Annunziata et al., "Phase 1 open-label study of MEDI-547 in patients with relapsed or refractory solid tumors," Invest New Drugs, Feb. 2013; 31(1): 77-84.
Aquino et al., "A biomimetic polyketide-inspired approach to small-molecule ligand discovery," Nature chemistry, Feb. 2012, 4(2):99-104.
Berge et al., "Pharmaceutical Salts," J Pharmaceutical Sciences, 1977, 66(1): 1-19.
Berlicki et al., "Unique a,J1- and a,a,J1,J1-Peptide Foldamers Based on cis-b-Aminocyclopentanecarboxylic Acid," Angew. Chem, Int. Ed., 2012, 51(9): 2208-2212.
Brantley-Sieders et al., "EphA2 receptor tyrosine kinase regulates endothelial cell migration and vascular assembly through phosphoinositide 3-kinase-mediated Rac1 GTPase activation," Journal of Cell Science, 2004, 117, 2037-49.
Brantley-Sieders et al., "Ephrin-A1 Facilitates Mammary Tumor Metastasis through an Angiogenesis-Dependent Mechanism Mediated by EphA Receptor and Vascular Endothelial Growth Factor in Mice," Cancer Res, 2006, 66(21 ):10315-10324.
Bycrofl et al., "A novel lysine-protecting procedure for continuous flow solid phase synthesis of branched peptides ," J. Chem. Soc., Chem. Commun., 1993, 9, 778-779.
Chen et al., "Bicyclic Peptide Ligands Pulled out of Cysteine-Rich Peptide Libraries," J. Am Chem. Soc., 2013, 135, (17): 6562-6569.
Cheng et al., "b-Peptides: From Structure to Function," Chem. Rev., 2001, 101(10): 3219-3232.
Darling et al. (Front Innnnunol. 2019; 10: 1473, 14 pages).
Diaz-Mochon et al., "Full Orthogonality between Ode and Fmoc: The Direct Synthesis of PNA-Peptide Conjugates," Org. Lett. 2004, 6(7): 1127-1129.
Fang et al., "A kinase-dependent role for EphA2 receptor in promoting tumor growth and metastasis," Oncogene 2005, 24, 7859-7868.
Heinis et al., "Phage-encoded combinatorial chemical libraries based on bicyclic peptides," Nat Chem Biol, 2009, 5, 502-507.
Horne et al., "Structural and biological mimicry of protein surface recognition by a/b-peplide foldamers," Proc. Natl., Acad. Sci., 2009, 106(35): 14751-14756.
Huang et al., "Amphiphilic Cyclic Peploids Tha1 Exhibit Antimicrobial Activity by Disrupting *Staphylococcus aureus* Membranes," Eur. J. Org., 2013, 2013(17): 3560-3566.
Karlsson et al., "Anlifungal Activity from 14-Helical b-Peptides," J. Am. Chem. Soc., 2006, 128(39): 12630-12631.
Klein, "Eph/ephrin signalling during development," Development, 2012, 139, 4105-4109.
Kodadek, "The rise, fall and reinvention of combinatorial chemistry," Chem. Commun., 2011, 47, 9757-9763.
Kritzer et al., "Helical---Peptide Inhibitors of the p53-hDM2 Interaction," J. Am. Chem. Soc., 2004, 126(31 ): 9468-9469.
Kubinyi (3D QSAR in Drug Design: Ligand-Protein Interactions and Molecular Similarity, vol. 2-3, Springer, 1998, 800 pages) p. 243-44 provided.

(Continued)

*Primary Examiner* — Robert H Havlin
(74) *Attorney, Agent, or Firm* — Fish & Richardson P.C.

(57) ABSTRACT

A one-bead-two-compound combinatorial synthesis technique provides libraries of macrocyclic peptidomimetic compounds and compositions with use as ligands for the Ephrin type-A receptor 2 (EphA2). The one-bead-two-compound technique and libraries of macrocyclic compounds are useful as research tools in drug discovery and/or to treat or prevent a range of diseases or disorders.

12 Claims, 9 Drawing Sheets

(56) References Cited

OTHER PUBLICATIONS

Lam et al., "The "One-Bead-One-Compound" Combinatorial Library Method," Chem. Rev., 1997, 97(2): 411-448.
Laursen et al., "b-Peploid Foldamers at Last," Acc. Chem. Res., 2015, 48(10): 2696-2704.
Lee et al., "Design and Facile Solid-Phase Synthesis of Conformationally Constrained Bicyclic Peploids," Org. Lett., 2011, 13(19): 5012-5015.
Li et al., "a-Aminoxy Acids: New Possibilities from Foldamers to Anion Receptors and Channels," Acc. Chem. Res., 2008, 41(10): 1428-1438.
Lian et al., "Cell-Permeable Bicyclic Peptide Inhibitors against Intracellular Proteins," J. Am. Chem. Soc 2014, 136(28): 9830-9833.
Lian et al., "Screening Bicyclic Peptide Libraries for Protein-Protein Interaction Inhibitors: Discovery of a Tumor Necrosis Factor-a Antagonist," J. Am. Chem. Soc., 2013, 13 5(32): 11990-11995.
Liu et al., "A Novel Peptide-Based Encoding System for "One-Bead One-Compound" Peptidomimetic and Small Molecule Combinatorial Libraries," J. Am. Chem. Soc 2002, 124(26): 7678-7680.
Lu et al., "EphA2 overexpression promotes ovarian cancer growth," Cancer Biol Ther., 2008, 7(7): 1098-1103.
Malkinson et al., "Efficient Solid-Phase-Based Total Synthesis of the Bisintercalator Tandem," J. Org, Chem., 2005 70(19): 7654-7661.
Miao et al., "EphA2 is a Mediator of Vemurafenib Resistance and a Novel Therapeutic Target in Melanoma," Cancer Discovery, 2015, 5(3): 274-287.
Nievergall et al., "Eph-dependent cell-cell adhesion and segregation in development and cancer," Cell. Mol. Life Sci., 2012, 69(11): 1813-1842.
Niu et al., "y-AApeptides: design, synthesis and evaluation," New J. Chem., 2011, 35, 542-545.
Paraiso et al., "Ligand independent EphA2 signaling drives the adoption of a targeted therapy-mediated metastatic melanoma phenotype," Cancer Discovery, 2015, 5(3): 264-273.
Pasquale, "Eph-Ephrin Bidirectional Signaling in Physiology and Disease," Cell, 2008, 133(1): 38-52.
Patch et al., "Mimicry of bioactive peptides via non-natural, sequence-specific peptidomimetic oligomers," Curr. Opin. Chem. Biol., Dec. 2002, 6(6): 872-877.
Qian et al., "Intracellular Delivery of Peptidyl Ligands by Reversible Cyclization: Discovery of a PDZ Domain Inhibitor that Rescues CFTR Activity," Angew. Chem. Int. Ed., 2015, 54(20): 5874-5878.
Richards et al., "Long Non-coding RNAs (LncRNA) Regulated by Transforming Growth Factor (TGF) b." J Biol Chem. 2015, 290, 6857-6867.
Seebach et al., "b-Peptidic Peptidomimetics," Acc. Chem. Res., 2008, 41(10): 1366-1375.
Shi et al., "y-AApeptides: Design, Structure, and Applications," Acc. Chem. Res., 2016, 49(3): 428-441.
Simpson et al., "A Cleavable Scaffold Strategy for the Synthesis of One-Bead One-Compound Cyclic Peptoid Libraries That Can Be Sequenced By Tandem Mass Spectrometry," Tetrahedron Lett., 2012, 53(18): 2341-2344.
Song et al., "A Novel and Rapid Encoding Method Based on Mass Spectrometry for "One-Bead-One-Compound" Small Molecule Combinatorial Libraries," J. Am. Chem. Soc., 2003, 125(20): 6180-6188.
Teng et al., "Identification of novel inhibitors that disrupt STAT3/DNA interaction from y-AApeptide OBOC combinatorial library," Chem. Commun., 2014, 50(63): 8739-8742.
Teng et al., "y-AApeptides as a New Class of Peptidomimetics," Chem. Eur. J., 2016, 22(16): 5458-5466.
Trader et al., "A Reversible and Highly Selective Inhibitor of the Proteasomal Ubiquitin Receptor Rpn13 Is Toxic to Multiple Myeloma Cells," J. Am. Chem. Soc., 2015, 137(19): 6312-6319.
Upadhyaya et al., "Inhibition of Ras signaling by blocking Ras-effector interactions with cyclic peptides," Angew. Chem. Int. Ed., 2015, 54(26): 7602-7606.
Wernnuth, The Practice of Medicinal Chennsitry, 2d ed. (2003), 768 pages. Chs 9-10 provided.
Wu et al., "Peptidomimetics," Acc. Chem. Res., 2008, 41(10): 1231-1232.
Wu et al., "y-AApeptide-based small-molecule ligands that inhibit Ab aggregation," Chem. Commun., May 2014, 50, 5206-5208.

YS-D-51-FITC         YS-D-52-FITC

YS-D-53-FITC         YS-D-54-FITC

ONE-BEAD-TWO-COMPOUND MACROCYCLIC LIBRARY AND METHODS OF PREPARATION AND USE

CROSS-REFERENCE TO RELATED APPLICATION

This application is a divisional of U.S. application Ser. No. 15/947,587, filed on Apr. 6, 2018, which claims the benefit of and priority to U.S. Provisional Application No. 62/483,038, filed on Apr. 7, 2017, the content of which are incorporated by reference herein in their entirety.

TECHNICAL FIELD

The invention relates to a novel one-bead-two-compound synthesis method to prepare combinatorial libraries of macrocyclic peptidomimetics.

BACKGROUND

The chemical biology and biomedical sciences are undergoing a new era of vigorous development due to the rapid discovery of new protein targets and unveiling of their biological importance. Combinatorial chemistry has emerged as a tool for the generation and screening of diverse libraries of compounds with potential use as ligands that recognize peptide or protein targets with high specificity and affinity. For example, combinatorial chemistry techniques have been applied to the preparation of peptide libraries with modular chemical diversity and favorable binding activity. Among them, macrocyclic peptides which have enhanced conformational constraint and binding affinity are widely recognized for exploring ligand-receptor interactions. Several general methods have been successfully developed to construct the macrocyclic ring systems.

Recent efforts have contributed to the creation of non-natural sequence-specific peptidomimetics. These peptidomimetics are developed based on the mimicry of peptide primary structure and modified peptide backbone for the introduction of diverse functional side chains. Compared with natural peptides, peptidomimetics possess enhanced protease-resistance and chemodiversity, as well as improved bioavailability. The past decade has witnessed significant progress in the development of biomimetic oligomers, including β-peptides, peptoids, α-aminoxy-peptides, α/β-peptides, azapeptides, etc. However, up to date only a handful of peptidomimetic libraries have been systematically investigated for protein ligand identification. The development of macrocyclic peptidomimetic combinatorial libraries is even more scarce. Thus, there remains an unmet need to identify macrocyclic peptidomimetic ligands that recognize peptide or protein targets with high specificity and affinity.

SUMMARY

The present invention provides macrocyclic peptidomimetic compounds and compositions, methods for their preparation and combinatorial libraries thereof, and use as ligands for the Ephrin type-A receptor 2 (EphA2). Libraries of macrocyclic compounds are useful as research tools in drug discovery and/or to treat or prevent a range of diseases or disorders.

In one aspect, the invention provides compounds or compositions of formula (I)

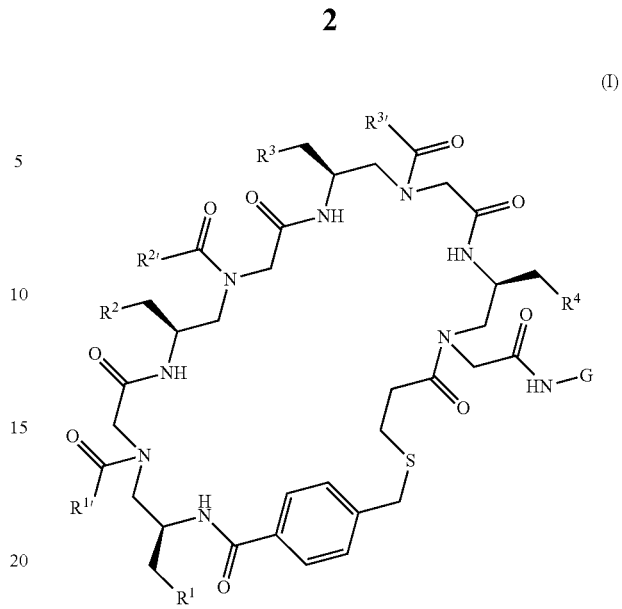

or a salt thereof, wherein:

$R^1$, $R^2$, $R^3$, $R^4$, $R^{1'}$, $R^{2'}$, and $R^{3'}$ are each independently selected from the group consisting of hydrogen, $C_{1-6}$alkyl, $C_{1-6}$haloalkyl, -$L^1$-$G^1$, -$L^1$-OH, -$L^1$-$NH_2$, -$L^1$-NH($C_{1-4}$alkyl), -$L^1$-N($C_{1-4}$alkyl)$_2$, -$L^1$-C(O)OH, -$L^1$-C(O)O$C_{1-4}$alkyl, -$L^1$-C(O)$NH_2$, -$L^1$-C(O)NH($C_{1-4}$alkyl), and -$L^1$-C(O)N($C_{1-4}$ alkyl)$_2$;

G is H or a solid support, the solid support being optionally substituted with a peptide sequence coding for $R^1$, $R^2$, $R^3$, $R^4$, $R^{1'}$, $R^{2'}$, and $R^{3'}$;

$L^1$ is a bond or a $C_{1-4}$alkylene; and $G^1$ is $C_{3-8}$cycloalkyl, aryl, a 4- to 12-membered heterocyclyl, or a 5- to 12-membered heteroaryl, wherein $G^1$ is optionally substituted with 1-4 substituents independently selected from the group consisting of $C_{1-4}$alkyl, $C_{1-4}$haloalkyl, halogen, cyano, —O$C_{1-4}$alkyl, —O$C_{1-4}$haloalkyl, oxo, and hydroxyl.

Another aspect of the invention provides pharmaceutical compositions comprising a pharmaceutically acceptable carrier and a compound of formula (I), wherein G is hydrogen, or a pharmaceutically acceptable salt thereof.

Another aspect of the invention provides a method of preparing a compound or composition of formula (I).

Another aspect of the invention provides a library or libraries of compounds or compositions according to formula (I) and methods for their preparation.

Another aspect provides methods for the identification of macrocyclic compounds that modulate a biological target.

Another aspect of the invention provides a method of treating a disease or disorder, such as cancer, which is mediated by EphA2 or characterized by EphA2 overexpression.

BRIEF DESCRIPTION OF THE FIGURES

FIG. 2A shows initial in vitro kinase assay and inhibition of EphA2 kinase activity by C-84. FIG. 2B shows that C-84 also suppresses the auto-catalytic activity of EphA2. FIG. 2C shows that the phosphorylation level of EphA2 is inhibited by C-84.

FIG. 3A shows the results of cell migration, and FIG. 3B shows the results of cell invasion.

DETAILED DESCRIPTION

1. Definitions

Figure 1:
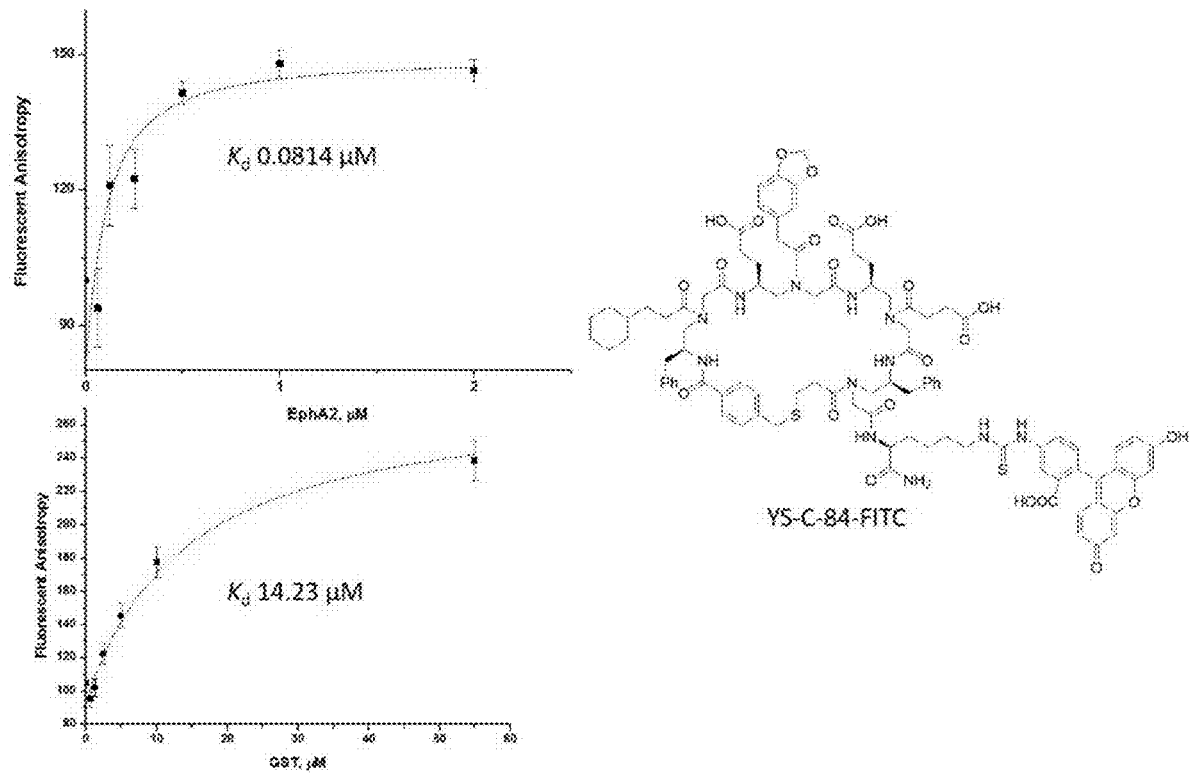
FIG. 1 illustrates the EphA2 binding activity ($K_d$) for a FITC hit.

The following definitions are provided as a general guide to understanding the claims and embodiments and are applicable where specific definitions are absent.

The term "γ-AApeptide" refers to the structure below, which mimics a dipeptide

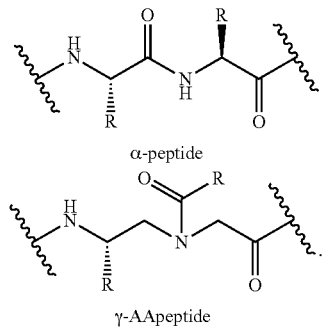

The γ-AApeptide as disclosed herein contains an N-terminal, as indicated by the

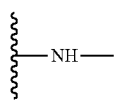

group in foregoing structure. The γ-AApeptide as disclosed herein contains a C-terminal, as indicated by the

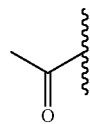

group in the foregoing structure.

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene," as used herein, means a divalent group derived from a straight or branched chain saturated hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and —CH$_2$CH(CH$_3$)CH(CH$_3$)CH$_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tertbutoxy, pentyloxy, and hexyloxy.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "halogen" means a chlorine, bromine, iodine, or fluorine atom.

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1,1-dimethylethyl, and the like.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "heteroaryl," as used herein, means an aromatic heterocycle, i.e., an aromatic ring that contains at least one heteroatom. A heteroaryl may contain from 5 to 12 ring atoms. A heteroaryl may be a 5- to 6-membered monocyclic heteroaryl or an 8- to 12-membered bicyclic heteroaryl. A 5-membered monocyclic heteroaryl ring contains two double bonds, and one, two, three, or four heteroatoms as ring atoms. Representative examples of 5-membered monocyclic heteroaryls include, but are not limited to, furanyl, imidazolyl, isoxazolyl, isothiazolyl, oxadiazolyl, oxazolyl, pyrazolyl, pyrrolyl, tetrazolyl, thiadiazolyl, thiazolyl, thienyl, and triazolyl. A 6-membered heteroaryl ring contains three double bonds, and one, two, three or four heteroatoms as ring atoms. Representative examples of 6-membered monocyclic heteroaryls include, but are not limited to, pyridinyl, pyridazinyl, pyrimidinyl, pyrazinyl, and triazinyl. The bicyclic heteroaryl is an 8- to 12-membered ring system having a monocyclic heteroaryl fused to an aromatic, saturated, or partially saturated carbocyclic ring, or fused to a second monocyclic heteroaryl ring. Representative examples of bicyclic heteroaryl include, but are not limited to, benzofuranyl, benzoxadiazolyl, 1,3-benzothiazolyl, benzimidazolyl, benzothienyl, indolyl, indazolyl, isoquinolinyl, naphthyridinyl, oxazolopyridine, quinolinyl, thienopyridinyl, 5,6,7,8-tetrahydroquinolinyl, and 6,7-dihydro-5H-cyclopenta[b]pyridinyl. The heteroaryl groups are connected to the parent molecular moiety through any substitutable carbon atom or any substitutable nitrogen atom contained within the groups.

The term "cycloalkyl" as used herein, means a monocyclic all-carbon ring containing zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups described herein can be appended to the parent molecular moiety through any substitutable carbon atom.

The terms "heterocycle" or "heterocyclic" refer generally to ring systems having at least one non-aromatic ring that contains at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic heterocycle, a fused bicyclic heterocycle, or a spiro heterocycle. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1, 1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, 1,3-benzodioxolyl, 1,3-benzodithiolyl, 3-azabicyclo[3.1.0] hexanyl, hexahydro-1H-furo[3,4-c]pyrrolyl, 2,3-dihydro-1, 4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. Spiro heterocycle means a 4, 5-, 6-, 7-, or 8-membered monocyclic heterocycle ring wherein two of the substituents on the same carbon atom form a second ring having 3, 4, 5, 6, 7, or 8-members. Examples of a spiro heterocycle include, but are not limited to, 1,4-dioxa-8-azaspiro[4.5]decanyl, 2-oxa-7-azaspiro[3.5]nonanyl, 2-oxa-6-azaspiro[3.3]heptanyl, and 8-azaspiro[4.5]decane. The monocyclic heterocycle groups of the present invention may contain an alkylene bridge of 1, 2, or 3 carbon atoms, linking two nonadjacent atoms of the group. Examples of such a bridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The monocyclic, fused bicyclic, and spiro heterocycle groups are connected to the parent molecular moiety through any substitutable carbon atom or any substitutable nitrogen atom contained within the group.

The term "oxo" as used herein refers to an oxygen atom bonded to the parent molecular moiety by a double bond. An oxo may be attached to a carbon atom or a sulfur atom by a double bond. Alternatively, an oxo may be attached to a nitrogen atom by a single bond, i.e., an N-oxide.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "protecting group" refers to a moiety that prevents chemical reactions from occurring on a heteroatom (such as, N, O, or S) to which that protecting group is attached. Various protecting groups are well known in the art and include those described in detail in Greene's Protective Groups in Organic Synthesis, T. W. Greene and P. G. M. Wuts, 4th edition, John Wiley & Sons, 2007, the entirety of which is incorporated herein by reference. For example, suitable amino protecting groups include, but are not limited to, carbobenzyloxy (—NHCO—OCH$_2$C$_6$H$_5$ or —NH-Cbz); t-butyloxycarbonyl (—NHCO—OC(CH$_3$)$_3$ or —NH-Boc); 9-fluorenylmethyloxycarbonyl (—NH-Fmoc), 2,2,2-trichloroethyloxycarbonyl (—NH-Troc), and allyloxycarbonyl (—NH-Alloc). In each of the foregoing, the —NH— represents the nitrogen from the amino group that is being protected.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric and zwitterionic forms of the compounds of the invention are within the scope of the invention.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

As used herein, "treat," "treating" and the like means a slowing, stopping or reversing of progression of cancer when provided a composition described herein to an appropriate control subject. The term also means a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease.

As used herein, "subject" or "patient" means an individual having symptoms of, or at risk for, a disease or disorder (such as cancer or other malignancy). A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

2. Compounds

In one aspect, provided herein are compounds or compositions of formula (I)

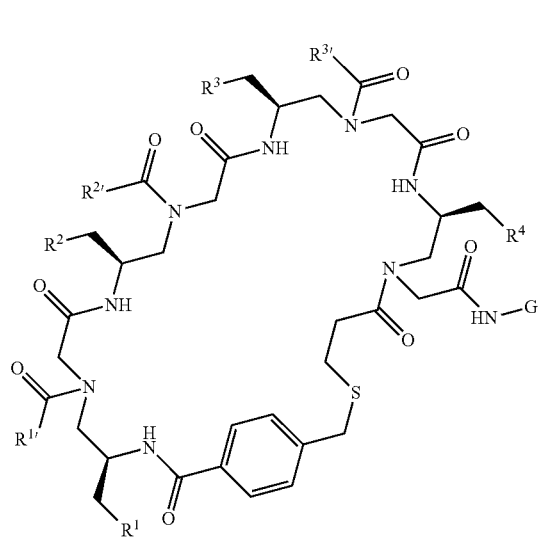

(I)

or a salt thereof, wherein:
$R^1$, $R^2$, $R^3$, $R^4$, $R^{1'}$, $R^{2'}$, and $R^{3'}$ are each independently selected from the group consisting of hydrogen, $C_{1-6}$alkyl, $C_{1-6}$haloalkyl, -$L^1$-$G^1$, -$L^1$-OH, -$L^1$-NH$_2$, -$L^1$-NH($C_{1-4}$alkyl), -$L^1$-N($C_{1-4}$alkyl)$_2$, -$L^1$-C(O)OH, -$L^1$-C(O)O$C_{1-4}$alkyl, -$L^1$-C(O)NH$_2$, -$L^1$-C(O)NH($C_{1-4}$alkyl), and -$L^1$-C(O)N($C_{1-4}$alkyl)$_2$;

G is H or a solid support, the solid support being optionally substituted with a peptide sequence coding for $R^1$, $R^2$, $R^3$, $R^4$, $R^{1'}$, $R^{2'}$, and $R^{3'}$;
$L^1$ is a bond or a $C_{1-4}$alkylene; and
$G^1$ is $C_{3-8}$cycloalkyl, aryl, a 4- to 12-membered heterocyclyl, or a 5- to 12-membered heteroaryl, wherein $G^1$ is optionally substituted with 1-4 substituents independently selected from the group consisting of $C_{1-4}$alkyl, $C_{1-4}$haloalkyl, halogen, cyano, —O$C_{1-4}$alkyl, —O$C_{1-4}$haloalkyl, oxo, and hydroxyl.

In some embodiments, $R^1$, $R^2$, $R^3$, $R^4$, $R^{1'}$, $R^{2'}$, and $R^{3'}$ are each independently selected from the group consisting of hydrogen, $C_{1-6}$alkyl, -$L^1$-$G^1$, —$C_{1-4}$alkylene-NH$_2$, —$C_{1-4}$alkylene-NH($C_{1-4}$alkyl), —$C_{1-4}$alkylene-N($C_{1-4}$alkyl)$_2$, —$C_{1-4}$alkylene-C(O)OH, —$C_{1-4}$alkylene-C(O)O$C_{1-4}$alkyl, —$C_{1-4}$alkylene-C(O)NH$_2$, —$C_{1-4}$alkylene-C(O)NH($C_{1-4}$alkyl), and —$C_{1-4}$alkylene-C(O)N($C_{1-4}$alkyl)$_2$. In further embodiments, $R^1$, $R^2$, $R^3$, $R^4$, $R^{1'}$, $R^{2'}$, and $R^{3'}$ are each independently selected from the group consisting of hydrogen, $C_{1-6}$alkyl, -$L^1$-$G^1$, —$C_{1-4}$alkylene-NH$_2$, and —$C_{1-4}$alkylene-C(O)OH. In the foregoing embodiments, $L^1$ and $G^1$ are as defined elsewhere herein.

In other embodiments, $G^1$ is $C_{3-8}$cycloalkyl, phenyl, or a 4- to 12-membered heterocyclyl, wherein $G^1$ is optionally substituted with 1-4 substituents independently selected from the group consisting of $C_{1-4}$alkyl, $C_{1-4}$haloalkyl, halogen, cyano, —O$C_{1-4}$alkyl, —O$C_{1-4}$haloalkyl, oxo, and hydroxyl. In further embodiments, $G^1$ is $C_{3-8}$cycloalkyl, phenyl, or a 4- to 8-membered monocyclic heterocycle, or a 7- to 12-membered bicyclic heterocycle having a monocyclic heterocycle fused to a phenyl. In still further embodiments, $G^1$ is $C_{3-8}$cycloalkyl, phenyl, or a 7- to 12-membered bicyclic heterocycle having a monocyclic heterocycle fused to a phenyl. In still further embodiments, $G^1$ is $C_{3-8}$cycloalkyl, phenyl, or 1,3-benzodioxolyl (e.g., 1,3-benzodioxol-5-yl). In the foregoing embodiments, $L^1$, $R^1$, $R^2$, $R^3$, $R^4$, $R^{1'}$, $R^{2'}$, and $R^{3'}$ are as defined elsewhere herein.

In other embodiments, $R^1$ is hydrogen, aryl, $C_{1-6}$alkyl, or —$C_{1-4}$alkylene-NH$_2$; $R^{1'}$ is —$C_{1-4}$alkylene-NH$_2$ or —$C_{1-4}$alkylene-$G^1$, where $G^1$ is $C_{3-8}$cycloalkyl or aryl; $R^2$ is —$C_{1-4}$alkylene-C(O)OH, aryl, or $C_{1-6}$alkyl; $R^{2'}$ is —$C_{1-4}$alkylene-NH$_2$ or —$C_{1-4}$alkylene-$G^1$, where $G^1$ is $C_{3-8}$cycloalkyl, aryl, or a 4- to 12-membered heterocyclyl; $R^3$ is hydrogen or —$C_{1-4}$alkylene-C(O)OH; $R^{3'}$ is —$C_{1-4}$alkylene-NH$_2$, —$C_{1-4}$alkylene-C(O)OH, or —$C_{1-4}$alkylene-$G^1$, where $G^1$ is aryl or a 4- to 12-membered heterocyclyl; and $R^4$ is hydrogen, $C_{1-6}$alkyl, —$C_{1-4}$alkylene-C(O)OH, or aryl.

In still further embodiments, $R^1$ is aryl; $R^{1'}$ is —$C_{1-4}$alkylene-$C_{3-8}$cycloalkyl; $R^2$ is —$C_{1-4}$alkylene-C(O)OH; $R^{2'}$ is —$C_{1-4}$alkylene-$G^1$, where $G^1$ is a 4- to 12-membered heterocyclyl; $R^3$ is —$C_{1-4}$alkylene-C(O)OH; $R^{3'}$ is —$C_{1-4}$alkylene-C(O)OH; and $R^4$ is aryl. In yet further embodiments, $R^1$ is phenyl; $R^{1'}$ is —$C_{1-4}$alkylene-$C_{3-8}$cycloalkyl; $R^2$ is —$C_{1-4}$alkylene-C(O)OH; $R^{2'}$ is —$C_{1-4}$alkylene-$G^1$, where $G^1$ is a 4- to 12-membered heterocyclyl; $R^3$ is —$C_{1-4}$alkylene-C(O)OH; $R^{3'}$ is —$C_{1-4}$alkylene-C(O)OH; and $R^4$ is aryl. According to the foregoing embodiments, are further embodiments where the 4- to 12-membered heterocyclyl is a 1,3-benzodioxolyl.

In some embodiments according to the foregoing, compounds of the invention have formula (I) where G is hydrogen and $R^1$, $R^2$, $R^3$, $R^4$, $R^{1'}$, $R^{2'}$, and $R^{3'}$ are as defined herein.

A preferred compound of the invention is

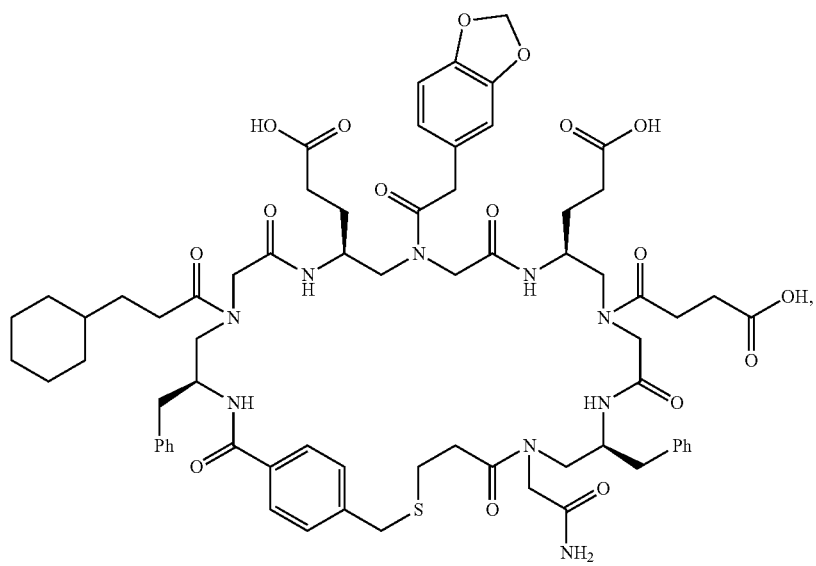 [SMILES: NC(=O)CN1C[C@H](Cc2ccccc2)NC(=O)CN(C(=O)CCC(=O)O)C[C@H](CCC(=O)O)NC(=O)CN(C(=O)Cc2ccc3c(c2)OCO3)C[C@H](CCC(=O)O)NC(=O)CN(C(=O)CCC2CCCCC2)C[C@H](Cc2ccccc2)NC(=O)c2ccc(cc2)CSCCC1=O]

which is referred to herein as compound "YS-C-84" or "C-84."

In other embodiments, G is a solid support, the solid support being optionally substituted with a peptide sequence coding for $R^1$, $R^2$, $R^3$, $R^4$, $R^{1'}$, $R^{2'}$, and $R^{3'}$. In some embodiments, the solid support has an interior portion and an exterior portion, the peptide sequence being attached to the interior portion and the macrocyclic peptidomimetic portion of formula (I) being attached to the exterior portion. In some embodiments, the peptide sequence and the macrocyclic peptidomimetic portion of formula (I) are independently attached to amino groups located, respectively, on the interior portion and the exterior portion of the solid support.

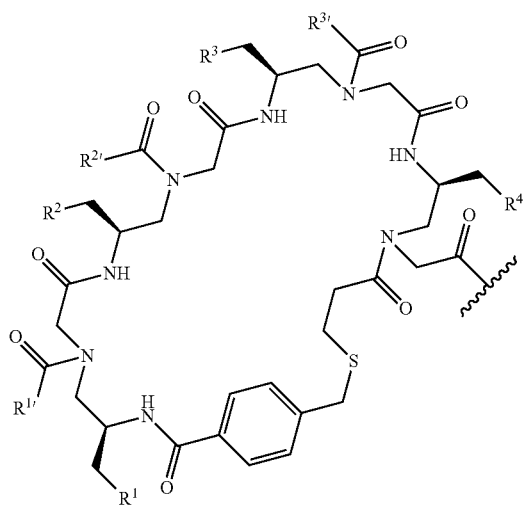

In other embodiments, G is a solid support in the form of a bead, such as a resin containing —NH$_2$ functional groups. Suitable beads include gelatinous resins used as support for solid phase synthesis. Examples of resins include those constructed with a backbone of low crosslinked polystyrene grafted with polyoxyethylene (polyethylene glycol), such as TentaGel® S NH2 resins (RAPP Polymere, Tuebingen, Germany).

In some embodiments, G is a solid support, and the compound or composition of formula (I) has a structure of formula (II)

(II)

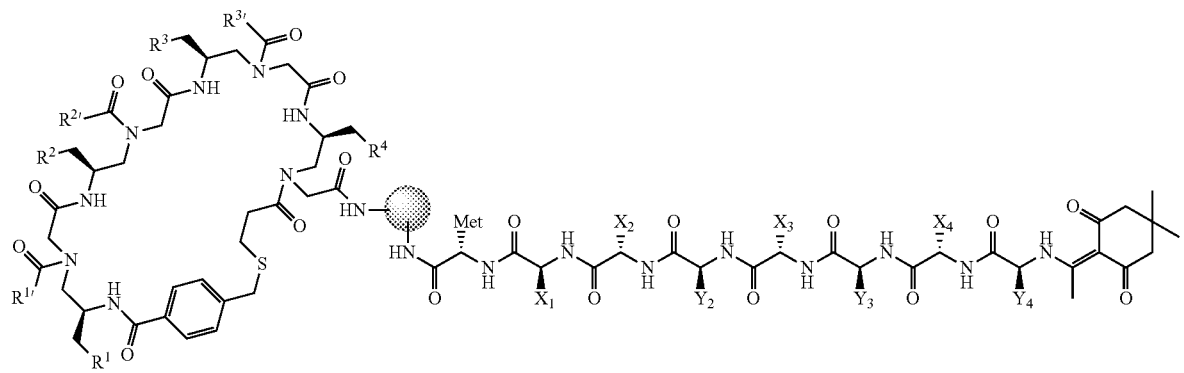

wherein:

⬤ is the solid support;

$R^1$, $R^2$, $R^3$, $R^4$, $R^{1\prime}$, $R^{2\prime}$, and $R^{3\prime}$ are defined herein under formula (I);

$X_1$ is a peptide side chain that codes for $R^4$;
$X_2$ is a peptide side chain that codes for $R^3$;
$X_3$ is a peptide side chain that codes for $R^2$;
$X_4$ is a peptide side chain that codes for $R^1$;
$Y_2$ is a peptide side chain that codes for $R^{3\prime}$;
$Y_3$ is a peptide side chain that codes for $R^{2\prime}$; and
$Y_4$ is a peptide side chain that codes for $R^{1\prime}$,
wherein $R^1$, $R^2$, $R^3$, $R^4$, $R^{1\prime}$, $R^{2\prime}$, $R^{3\prime}$, $X_1$, $X_2$, $X_3$, $X_4$, $Y_2$, $Y_3$, and $Y_4$ are as defined herein.

In some embodiments, the compound or composition has a structure of formula (II), wherein each of $R^1$, $R^2$ and $R^3$, and $R^4$ is independently hydrogen,

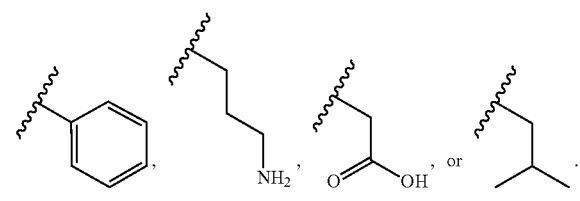

In some embodiments, the compound or composition has a structure of formula (II), wherein each of $R^{1\prime}$, $R^{2\prime}$, and $R^{3\prime}$ is independently

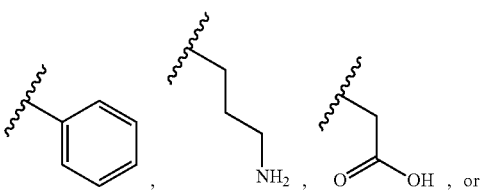

-continued

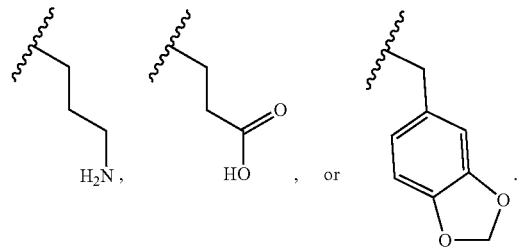

In some embodiments, the compound or composition has a structure of formula (II), wherein each of $R^1$, $R^2$, and $R^3$, and $R^4$ is independently H,

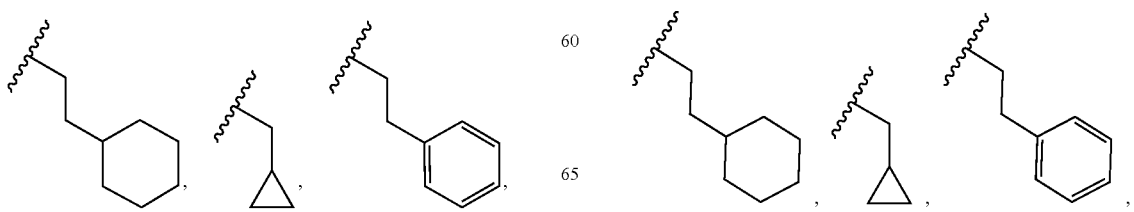

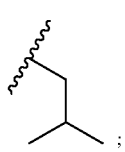

and wherein each of $R^{1\prime}$, $R^{2\prime}$, and $R^{3\prime}$ is independently,

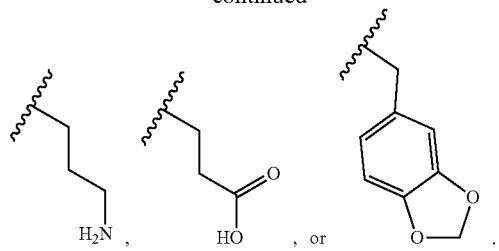

In some embodiments, each of the coding peptide side chains ($X_1$, $X_2$, $X_3$, $X_4$, $Y_2$, $Y_3$, and $Y_4$) corresponds to a particular group on the macrocyclic peptidomimetic portion of formula (II) ($R^1$, $R^2$, $R^3$, $R^4$, $R^{1'}$, $R^{2'}$, and $R^{3'}$). In some embodiments, the choice of amino acids in coding peptide chain is based on the physical properties of the side chains, such as the properties of being positively charged, negatively charged, or hydrophobic. For example, a coding map is provided in Table 1 below.

3. Library Synthesis

In another aspect, provided herein are libraries of compounds or compositions according to formula (I). In some embodiments, the library disclosed herein comprises a plurality of compounds or compositions of formula (I), wherein G is a solid support. In some embodiments, the library disclosed herein comprises a plurality of compounds or compositions of formula (II), in which $R^1$, $R^2$, $R^3$, $R^4$, $R^{1'}$, $R^{2'}$, $R^{3'}$, $X_1$, $X_2$, $X_3$, $X_4$, $Y_2$, $Y_3$, and $Y_4$ are as defined herein.

In another aspect, provided herein are methods of preparing a library of compounds or compositions according to formula (I), wherein G is a solid support having a —NH$_2$ group, the method comprising:

(a) attaching a first γ-AApeptide building block to the —NH$_2$ group of the solid support, the first γ-AApeptide building block comprising $R^4$ and a

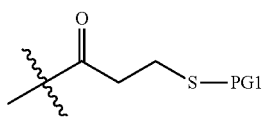

group, wherein PG1 is a protecting group;

(b) attaching a second γ-AApeptide building block to the N-terminal of the first γ-AApeptide building block, the second γ-AApeptide building block comprising $R^3$ and $R^{3'}$;

(c) attaching a third γ-AApeptide building block to the N-terminal of the second γ-AApeptide building block, the third γ-AApeptide building block comprising $R^2$ and $R^{2'}$;

(d) attaching a fourth γ-AApeptide building block to the N-terminal of the third γ-AApeptide building block, the fourth γ-AApeptide building block comprising $R^1$ and $R^{1'}$;

(e) reacting the N-terminal of the fourth γ-AApeptide building block with

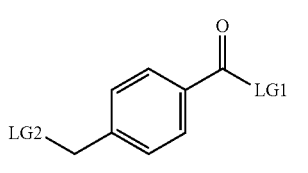

to produce an intermediate having a

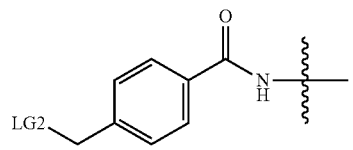

group, wherein each of LG1 and LG2 is a leaving group; and (f) removing PG1 and allowing the resulting intermediate to cyclize to produce the compound or formula (I).

PG1 may be a known protecting group to protect a thiol (—SH) group, such as those described in Greene's Protective Groups in Organic Synthesis, T. W. Greene and P. G. M. Wuts, 4$^{th}$ edition, John Wiley & Sons, 2007. In some embodiments, PG1 is —CR$^a$R$^b$R$^c$, wherein R$^a$, R$^b$, and R$^c$ are each independently $C_{1-6}$alkyl, aryl, aryl substituted with one or more —O—$C_{1-4}$alkyl, or $C_{1-4}$alkylene-aryl. In some embodiments, PG1 is triphenylmethyl (trityl or —CPh$_3$), 4,4'-dimethoxytrityl, p-methylbenzyl, or acetamidomethyl. In some embodiments, PG1 is 4,4'-dimethoxytrityl.

In some embodiments, LG1 and LG2 are each independently a leaving group known in the art, such as halogen or tosylate (p-toluenesulfonyl-O— or TsO—). In some embodiments, LG1 and LG2 are each independently halogen. For example, in some embodiments, LG1 is chloro, and LG2 is bromo.

In some embodiments, the method disclosed herein may be used to prepare a library comprising a plurality of compounds or compositions of formula (I), wherein each of $R^1$, $R^2$, and $R^3$, and $R^4$ is independently H,

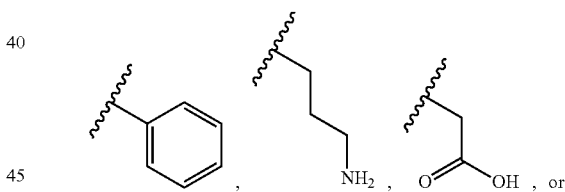

and wherein each of $R^{1'}$, $R^{2'}$, and $R^{3'}$ is independently

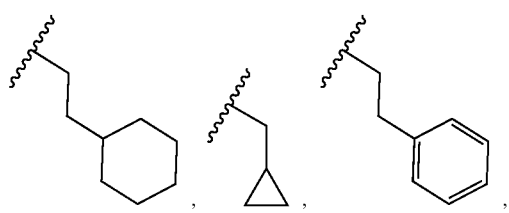

-continued

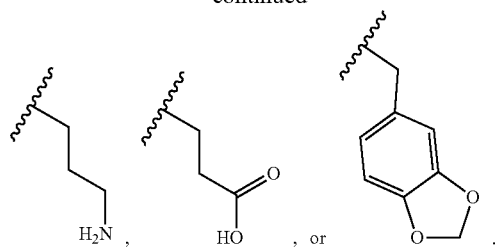

Each "attaching" process in steps (a), (b), (c), (d), and (e) above may comprise a single reaction or multiple reactions. Each of the γ-AApeptide building blocks may contain additional protecting groups, such as protecting groups for —NH₂ or —NH—. Examples of N-protecting groups for the γ-AApeptide building blocks include, but are not limited to Boc, Fmoc, Cbz, and the Alloc group (CH$_2$=CH—O—CO—). The choice of these additional protecting groups and their removal during the process of preparing the libraries disclosed herein are within the knowledge of the art.

In some embodiments, libraries of compounds according to the invention may be prepared using the methods generally illustrated in Scheme 1. The library design includes introducing a Dmt (Dmt=4,4'-dimethoxytrityl) protected mercaptoethyl carbonyl group to the secondary amine in the first γ-AApeptide building block (Scheme 1) on the solid phase. After another three γ-AApeptide building blocks are assembled, a 4-(bromomethyl)benzoyl group is attached to the N-terminal amino group of the sequence. The Dmt protecting group may be selectively removed by 2% TFA in DCM without affecting protecting groups of other side chains. After the removal of the Dmt group, the γ-AApeptide may be cyclized under nearly neutral conditions. Given that one side chain is dedicated to cyclization, this class of 4-building-block cyclic γ-AApeptides would possess 7 variable side chains. Due to the structural nature of γ-AApeptides, 4 chiral side chains (R, Scheme 1), come from the side chains of 5 different types of the N-Alloc protected γ-AApeptide building blocks [Ala, Phe, Lys, Glu, Leu]. The other three side chains (R¹, Scheme 1) are introduced by acylating the secondary amino group with 6 kinds of carboxylic acid or acyl chlorides after deprotection of the alloc group. Thus, by using the split and pool method, the theoretical diversity of the library is expected to be 135,000.

Scheme 1. The cyclization strategy of the library.

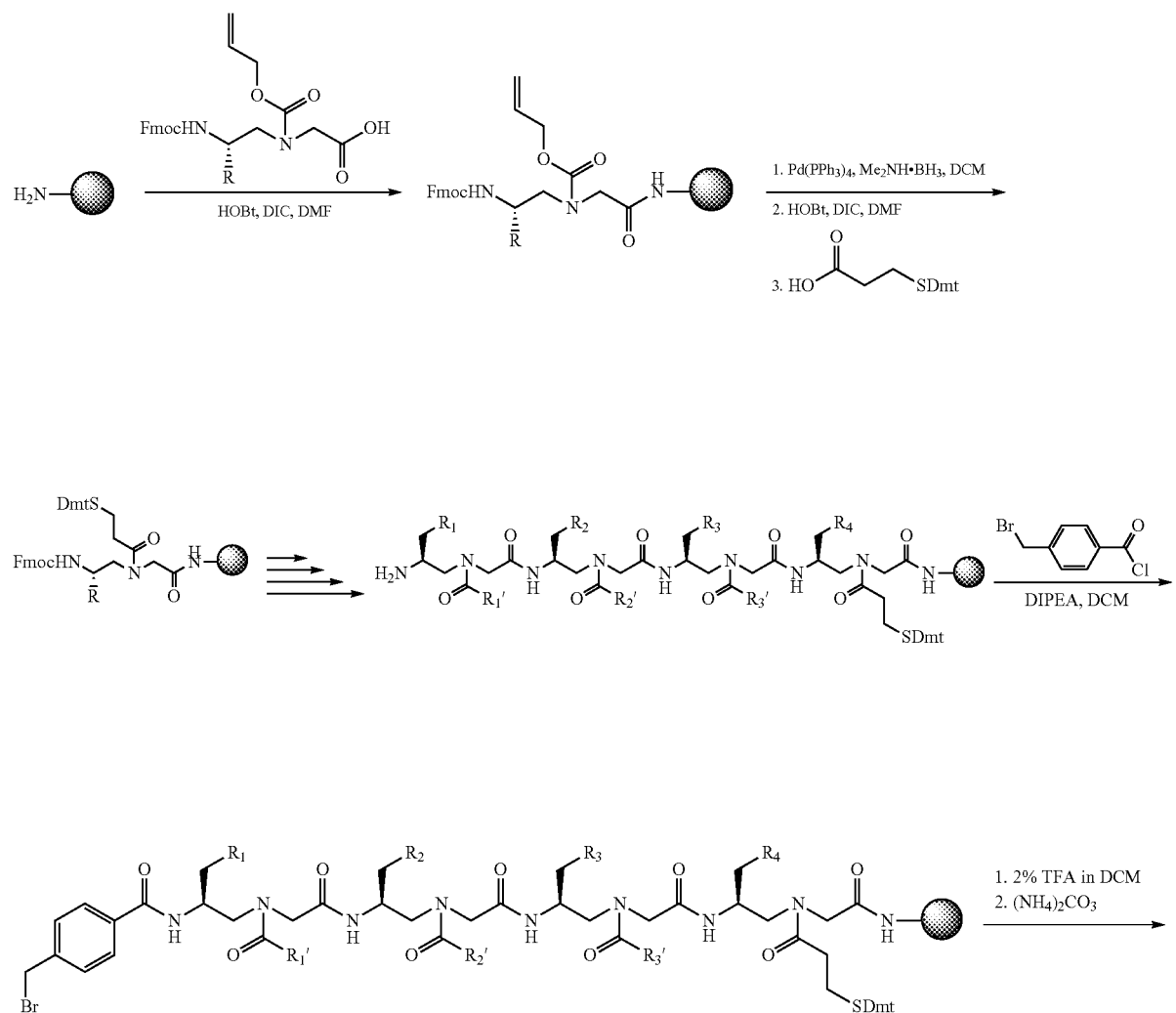

-continued

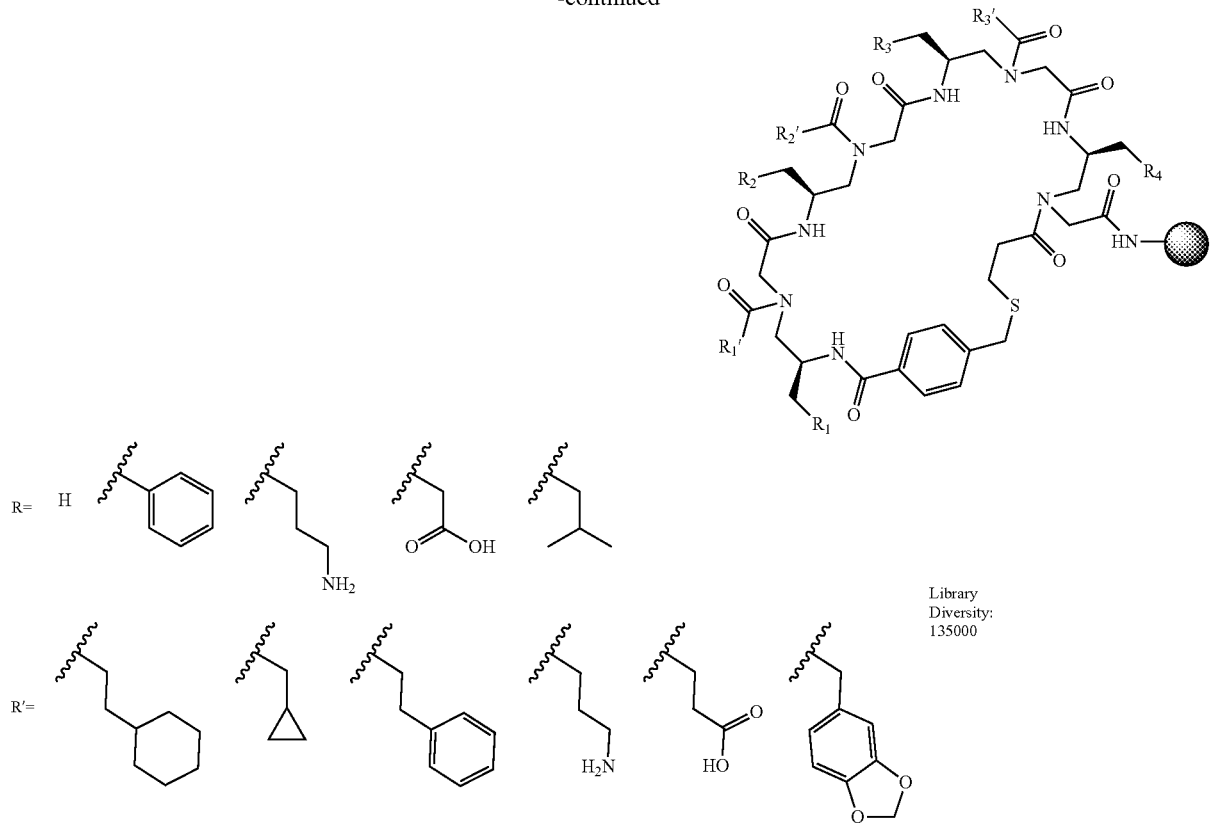

Library Diversity: 135000

To sequence the cyclic γ-AApeptides, a one-bead-two-compound (OBTC) library strategy was developed where both ligands and analyzable coding sequences are contained on the same bead. Peptides consisting of α-amino acids may serve as coding sequences since the MS/MS pattern of amino acid fragments is unambiguous. However, previous approaches for the construction of peptide coding sequence were found to be incompatible with the chemistry used in the preparation of cyclic γ-AApeptide library. This was because Fmoc, alloc and trityl chemistry all had been utilized for the synthesis of cyclic γ-AApeptides. To overcome these difficulties, synthesis of coding peptides may be carried out by using Dde ((1-(4,4-dimethyl-2,6-dioxacyclohexylidene)ethyl) protected α-amino acids. The deprotection of Dde is very mild using $NH_2OH \cdot HCl$ and imidazole and fully orthogonal to chemistry engaged in the synthesis of thioether-bridged cyclic γ-AApeptides.

In another aspect, provided herein are methods of preparing a library of compounds or compositions of formula (II), the method comprising the steps of:

(a) providing a starting solid support

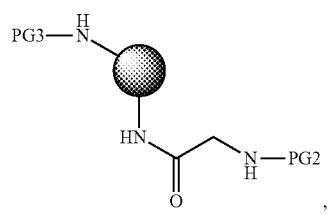

wherein PG2 and PG3 are each a protecting group;

(b) removing PG2 and attaching a first amino acid unit comprising $X_1$ to the N atom protected by PG2;

(c) removing PG3 and attaching a first γ-AApeptide building block to the N atom protected by PG3, the first γ-AApeptide building block comprising $R^4$ and a

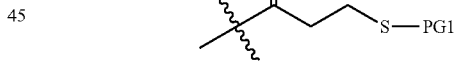

group, wherein PG1 is a protecting group;

(d)(1) attaching a second amino acid unit comprising $X_2$ to the first amino acid unit; (d)(2) attaching a second γ-AApeptide building block comprising $R^3$ to the N-terminal of the first γ-AApeptide building block; (d)(3) attaching a third amino acid unit comprising $Y_2$ to the second amino acid unit; (d)(4) attaching R3' to the second γ-AApeptide building block;

(e) repeating steps (d)(1)-(d)(4) two more times, resulting in the attachment of a third γ-AApeptide building block comprising $R^2$ and $R^{2'}$, a fourth γ-AApeptide building block comprising $R^1$ and $R^{1'}$, a fourth amino acid unit comprising $X_3$, a fifth amino acid unit comprising $Y_3$, a sixth amino acid unit comprising $X_4$, and a seventh amino acid unit comprising $Y_4$;

(f) reacting the N-terminal of the fourth γ-AApeptide building block with

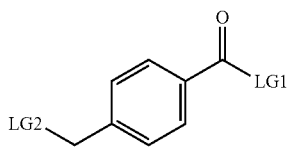

to produce an intermediate having a

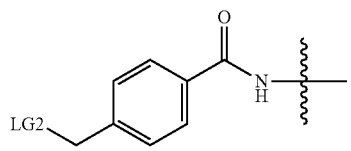

group, wherein each of LG1 and LG2 is a leaving group; and (g) removing PG1 and allowing the resulting intermediate to cyclize to produce the compound or formula (II);

wherein each of the amino acid units comprises —NH-PG4 before being attached to the reminder of the compound or composition, wherein PG4 is a protection group, and wherein the —NH-PG4 group is converted to —NH$_2$ before the attachment of the next amino acid unit.

PG1 may be a known protecting group to protect a thiol (—SH) group. In some embodiments, PG1 is —CR$^a$R$^b$R$^c$, wherein R$^a$, R$^b$, and R$^c$ are each independently C$_{1-6}$alkyl, aryl, aryl substituted with one or more —O—C$_{1-4}$alkyl, or C$_{1-4}$alkylene-aryl. In some embodiments, PG1 is triphenylmethyl (trityl or —CPh$_3$), 4,4'-dimethoxytrityl, p-methylbenzyl, or acetamidomethyl. In some embodiments, PG1 is 4,4'-dimethoxytrityl.

Each of PG2 and PG3 may be a suitable protecting group for —NH$_2$ known in the art. Examples of suitable N-protecting groups include, but are not limited to Boc, Fmoc, Cbz, and the Alloc group (CH$_2$=CH—O—CO—). In some embodiments, PG2 is Fmoc, and PG3 is Boc.

In some embodiments, LG1 and LG2 are each independently a leaving group known in the art, such as halogen or tosylate (p-toluenesulfonyl-O— or TsO—). In some embodiments, LG1 and LG2 are each independently halogen. For example, in some embodiments, LGs is chloro, and LG2 is bromo.

In some embodiments, PG4 is a protecting group for —NH$_2$, which can be removed under using NH$_2$OH.HCl and imidazole. In some embodiments, PG4 is 1-(4,4-dimethyl-2,6-dioxacyclohexylidene) ethyl (Dde or

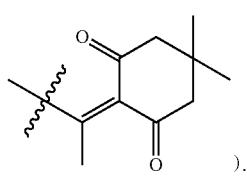 [SMILES: *C(C)=C1C(=O)CC(C)(C)CC1=O]

).

Each "attaching" process in steps (b), (c), (d1), (d2), (d3), and (d4) above may comprise a single reaction or multiple reactions. Each of the γ-AApeptide building blocks may contain additional protecting groups, such as protecting groups for —NH$_2$ or —NH—. Examples of N-protecting groups for the γ-AApeptide building blocks include, but are not limited to Boc, Fmoc, Cbz, and the Alloc group (CH$_2$=CH—O—CO—). The choice of these additional protecting groups and their removal during the process of preparing the libraries disclosed herein are within the knowledge of the art.

In some embodiments, the method disclosed herein may be used to prepare a library comprising a plurality of compounds or compositions of formula (II), wherein each of R$^1$, R$^2$, and R$^3$, and R$^4$ is independently H,

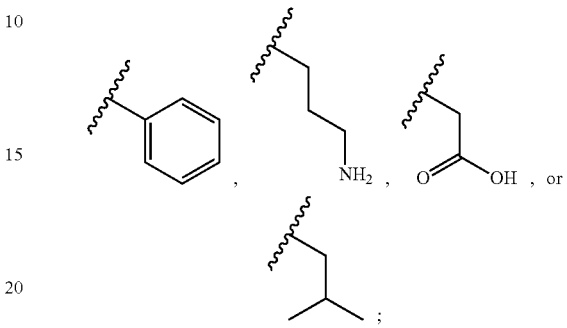

each of R$^{1'}$, R$^{2'}$, and R$^{3'}$ is independently

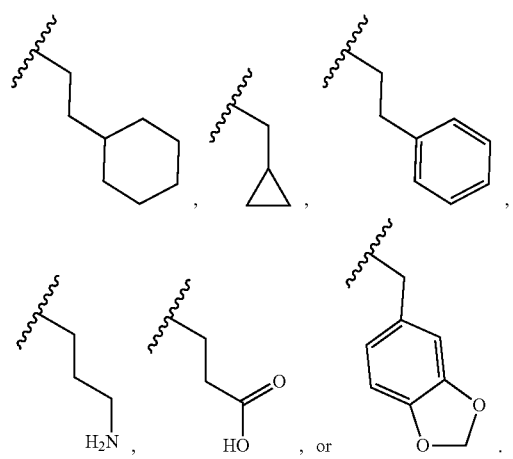

X$_1$ is a peptide side chain that codes for R$^4$; X$_2$ is a peptide side chain that codes for R$^3$; X$_3$ is a peptide side chain that codes for R$^2$; X$_4$ is a peptide side chain that codes for R$^1$; Y$_2$ is a peptide side chain that codes for R$^{3'}$; Y$_3$ is a peptide side chain that codes for R$^{2'}$; and Y$_4$ is a peptide side chain that codes for R$^{1'}$.

The library of compounds or compositions of formula (II) are also referred to as one-bead-two-compound (OBTC) cyclic γ-AApeptide combinatorial library, or cyclic γ-AA-peptide combinatorial library. In some embodiments, the cyclic γ-AApeptide combinatorial library as disclosed herein may be prepared as generally shown in Scheme 2. Briefly, TentaGel beads (200-250 µm; 1.5 nmol/bead) are soaked in water for overnight before being exposed to 1:1 (v/v) DCM/Et$_2$O containing 0.5 equiv di-tert-butyl dicarbonate (Boc$_2$O). This is expected to lead to Boc protection of amino groups on the outer surface of the beads since the interior of beads still remains in water. After wash with DMF, the interior of the beads is allowed to react with the Met, the amino acid facilitating coding peptide cleavage upon cyanogen bromide (CNBr) treatment.

After removal of the Fmoc protecting group, the beads are split into 5 equal aliquots and reacted with 5 different Dde protected amino acids respectively, so as to establish the coding tag representing the first γ-AApeptide building block on the outer layer. Subsequently, the Boc group of the outer layer is removed by TFA, followed by the attachment of 5 Alloc γ-AApeptide protected building blocks. Next, the Alloc group is removed by Pd(PPh$_3$)$_4$ and Me$_2$NH.BH$_3$, and the Dmt protected 3-mercaptopropanoic acid is added to react with the secondary amino group. The beads are pooled and split into 5 aliquots again.

After the Dde group is removed, the second set of the Dde protected amino acids is added to introduce the coding tag for the second γ-AApeptide building block on the outer layer of the beads. These steps were repeated for 3 more times. Compared with the cycle of the first building block, the only difference in the subsequent synthetic process on the outer layer is that after the Alloc group is removed, the N group of the γ-AApeptide building blocks are reacted with different carboxylic acid or acyl chlorides to introduce diverse side chains. Since each γ-AApeptide building block bears two side chains, two Dde protected amino acids are used to code each building block.

Finally, the 4-(bromomethyl)benzoyl chloride is used to cap the N-terminal of γ-AApeptides on the outer layer, followed by selective removal of the Dmt group on the thiol linker with 2% TFA in DCM. The cyclization of γ-AApeptides is achieved in the presence of (NH$_4$)$_2$CO$_3$, which occurs on the surface of the beads only due to the lack of cyclization linker in the interior of the beads. The deprotection of side chain protecting groups is conducted in 94% TFA, 2% Triisopropylsilane, 2% water and 2% Thioanisole (v:v:v:v). The quality of beads is excellent, as evidenced by the fact that 8 out 10 randomly selected beads show unambiguous MS/MS fragmentation pattern by MALDI and are able to provide the information of coding peptide sequence almost instantly.

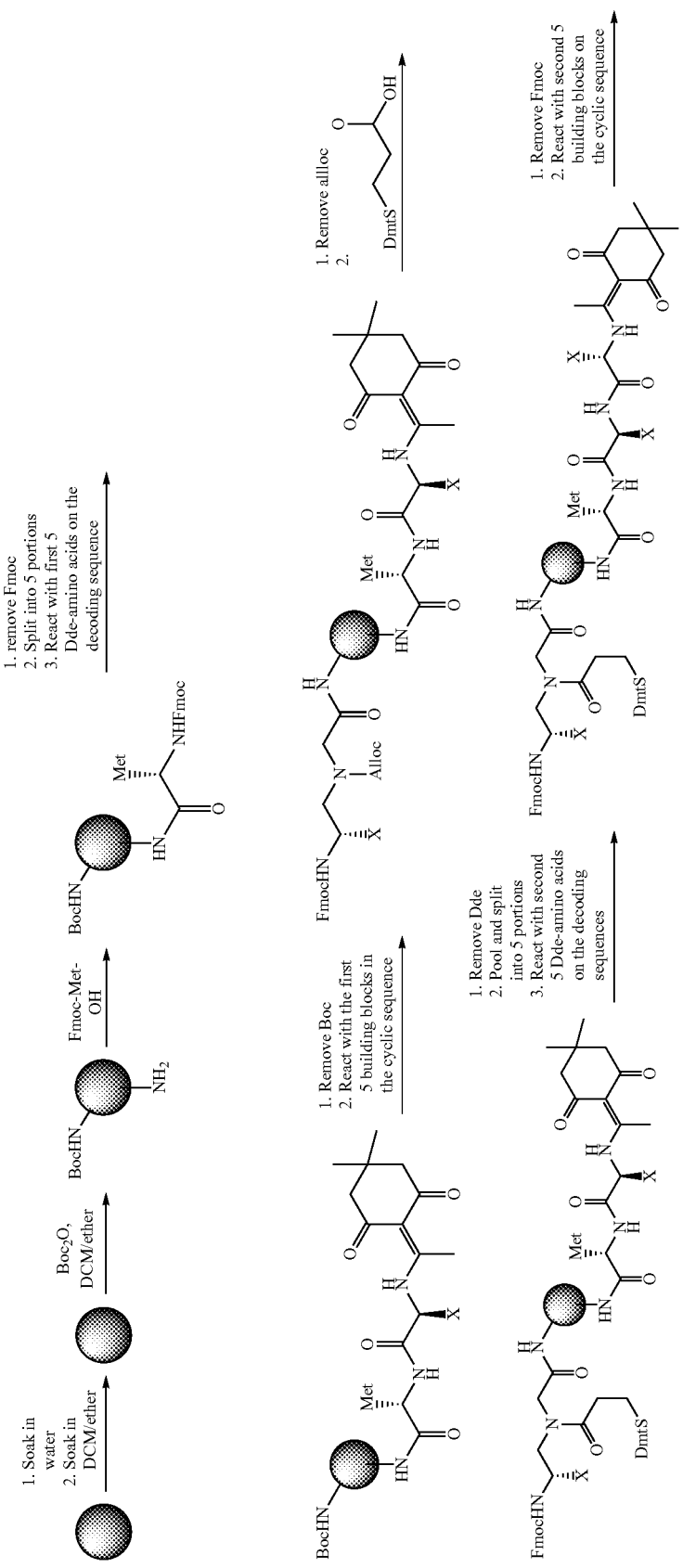
Scheme 2. Design and synthesis of thioether bridged macrocyclic γ-AApeptide library.

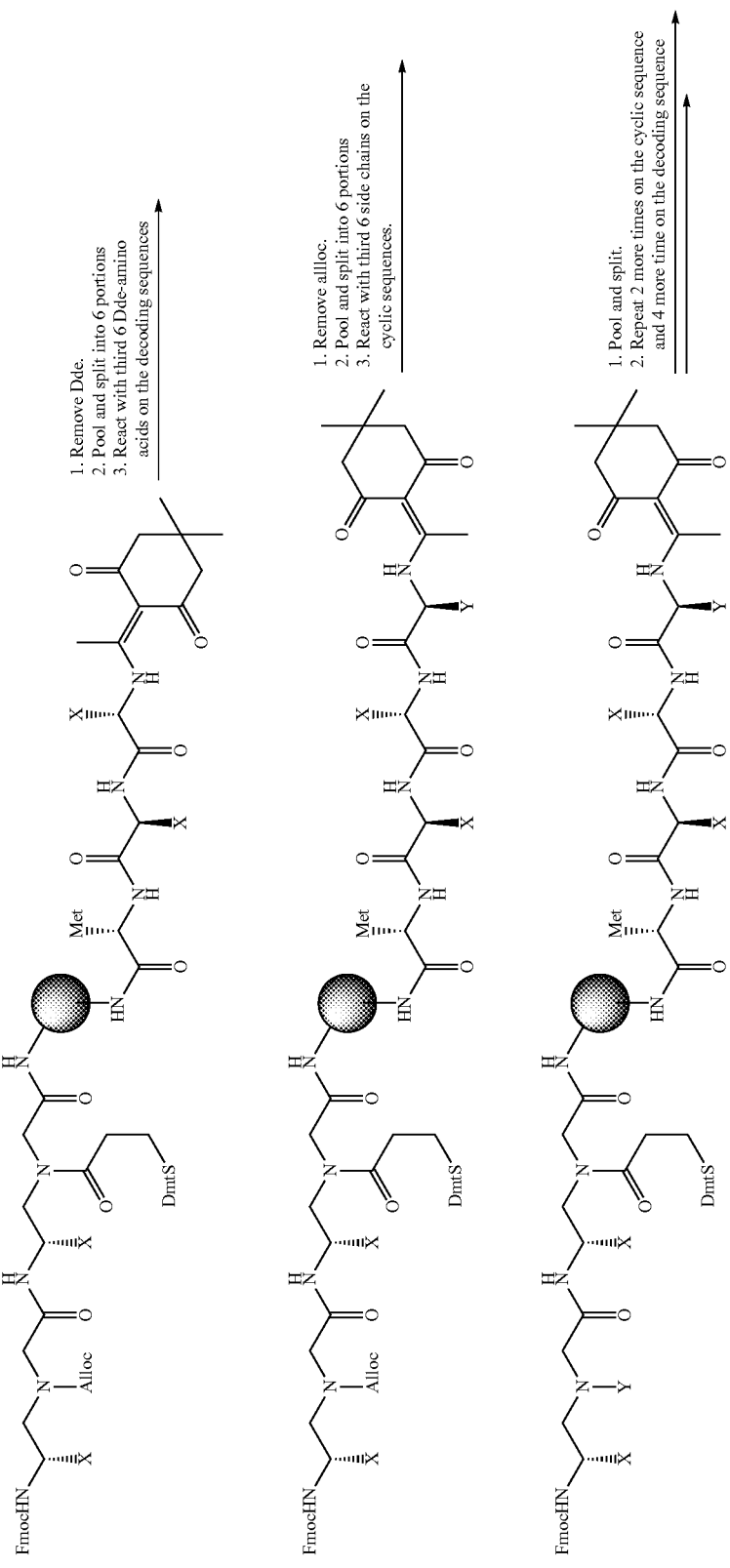

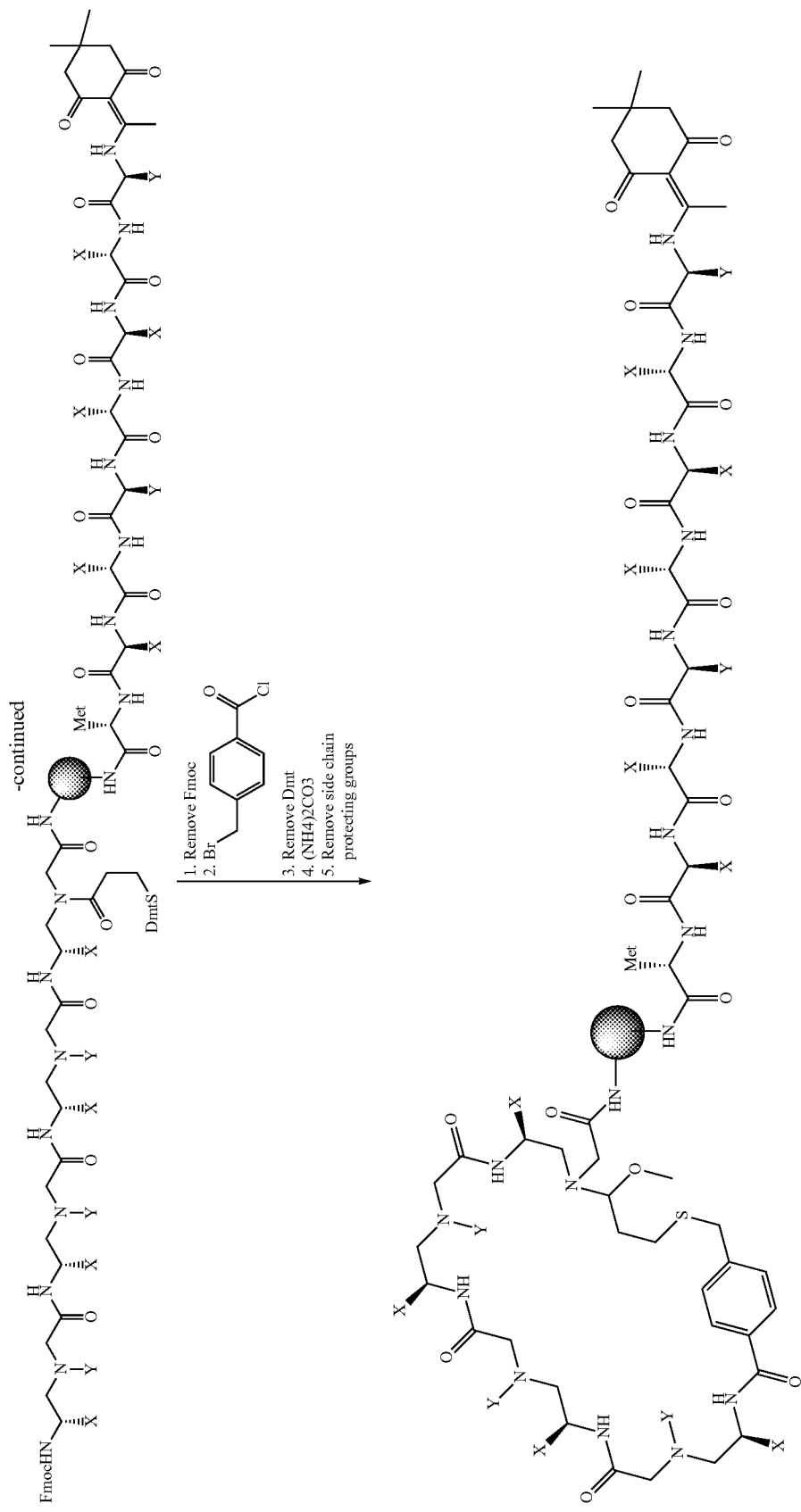

4. Method of Use

Library Screening and Analysis

A new class of macrocyclic peptidomimetic combinatorial library is disclosed herein. With the unique γ-AApeptide backbone which ensures the chemodiversity in the library, the method disclosed herein has great potential to be a rich source in protein/peptide ligands identification. When compared to previous linear peptide library, the thioether bridged macrocyclic γ-AApeptide library has the advantages such as significantly enhanced conformal rigidity of the backbones and cell permeability, leading to higher promise in the identification of more potent and useful ligands/molecular probes. The new encoding approach of Dde peptide tags greatly increases the possibility and ease of the structural elucidation of putative hits. Thus, the macrocyclic peptidomimetic combinatorial library disclosed herein may be used as a new platform for screening against various biological targets and/or therapeutic agents.

In one aspect, provided is a method of screening a library of compounds as disclosed herein for their biological activities. For example, such screen may be used for identifying ligands for a target protein. In some embodiments, provided is a method of screening for biological activity, the method comprising the steps of (a) contacting the library of compounds or compositions of formula (II) with a target protein or a fragment thereof, whereby one or more of the compounds and compositions bind to the target protein or fragment thereof to form a complex; and (b) detecting the target protein or fragment thereof in the complex of step (a).

In some embodiments, the screening method disclosed herein further comprises (c) isolating the complex of step (a);

(d) optionally isolating the coding peptide portion, or a part thereof, from the isolated complex of step (c); and (e) identifying one or more of the peptide side chains $X_1$, $X_2$, $X_3$, $X_4$, $Y_2$, $Y_3$, and $Y_4$.

In some embodiments, the target protein or fragment thereof is EphA2 protein, or fragment thereof, such as the intracellular domain of EphA2 protein. In some embodiments, the contacting of step (a) comprises incubation or mixing the library of compounds or compositions of formula (II) (having a solid support, such as beads) with the target protein in a buffer. The binding of the compounds or compositions of the library to the target protein or fragment thereof results in a complex formed by the protein and the compounds or compositions bound thereto. Following the contacting (e.g. incubation or mixing) of step (a), the solid support (e.g. beads) may be washed to remove the unbound protein.

The detection of step (b) may be accomplished by known methods for detecting proteins or fragments thereof. Suitable detection techniques include, but are not limited to nonspecific methods (such as light absorbance) or specific methods (such as various antibody-based methods). In some embodiments, the detection of step (b) includes the use of antibody against the target protein of proteins or fragment thereof, such as ELISA, immunoprecipitation, immunoelectrophoresis, westernblotting, and immunostaining. In some embodiments, the detection of step (b) includes the use of fluorescent microscopy.

In particular embodiments, the detection of step (b) comprises contacting the complex of step (a) with a primary antibody against the target protein or fragment thereof; contacting the resulting mixture with a secondary antibody against the primary antibody, the secondary antibody comprising a fluorophore; and detecting the fluorescent signals from the secondary antibody.

In some embodiments, the screening method disclosed herein further comprises isolating the complex formed by the target protein or the fragment thereof and the compounds or compositions bound thereto (step (c)). The isolation may be achieved by known techniques, such as micropipetting under a microscope.

The compounds or compositions of formula (II) contains a macrocyclic peptidomimetic portion

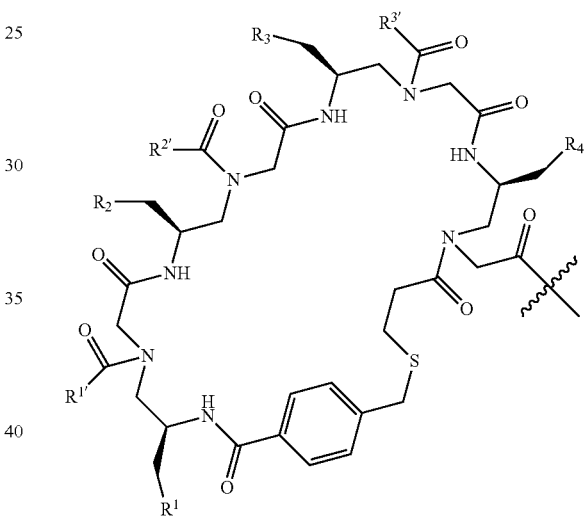

and a coding peptide portion,

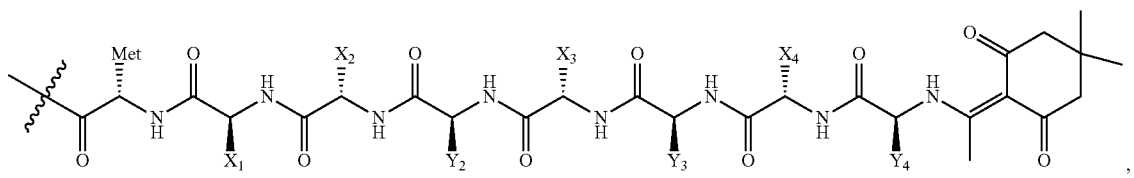

in which $X_1$ is a peptide side chain that codes for $R^4$; $X_2$ is a peptide side chain that codes for $R^3$; $X_3$ is a peptide side chain that codes for $R^2$; $X_4$ is a peptide side chain that codes for $R^1$; $Y_2$ is a peptide side chain that codes for $R^{3'}$; $Y_3$ is a peptide side chain that codes for $R^{2'}$; and $Y_4$ is a peptide side chain that codes for $R^{1'}$. In some embodiments, the screening method disclosed herein may optionally comprise isolating the coding peptide portion of the bound compound or composition, or a part thereof, from the complex with target protein (step (d)). In some embodiments, the coding peptide can be isolated in whole or in part by incubation with a cleaving agent, such as CNBr. In some embodiments, the isolated complex from step (c) may be incubated with guanidium chloride to denature any potential proteins bound to the surfaces of the solid support (such as beads), followed by treatment of CNBr to cleave the coding peptides from the solid support. In some embodiments, the coding peptide portion is not isolated from the isolated complex of step (c). In some embodiments, part of the coding peptide portion is isolated from the isolated complex of step (c). In some embodiments, the entire coding peptide portion is isolated from the isolated complex of step (c).

The sequence of the coding peptide side chains ($X_1$, $X_2$, $X_3$, $X_4$, $Y_2$, $Y_3$, and $Y_4$) contains structural information of the corresponding macrocyclic peptidomimetic compound (having the $R^1$, $R^2$, $R^3$, $R^4$, $R^{1'}$, $R^{2'}$, and $R^{3'}$ groups). In some embodiments, to elucidate the structure of the active macrocyclic peptidomimetic compound, the screening method disclosed herein further comprises identifying one or more of the peptide side chains $X_1$, $X_2$, $X_3$, $X_4$, $Y_2$, $Y_3$, and $Y_4$ (step (e)). The identity of the coding peptide side chains ($X_1$, $X_2$, $X_3$, $X_4$, $Y_2$, $Y_3$, and $Y_4$) can be identified by know technologies, such as mass spectrometry. In some embodiments, the coding peptides can be identified and sequenced by tandem MS/MS of MALDI mass spectrometer. In some embodiments, at least one of the coding peptide side chains is identified. In some embodiments, two or more of the coding peptide side chains are identified. In some embodiments, the side chains of a fragment of the coding peptide portion are identified. In some embodiments, the side chains of the entire coding peptide portion are identified.

Figure 12:
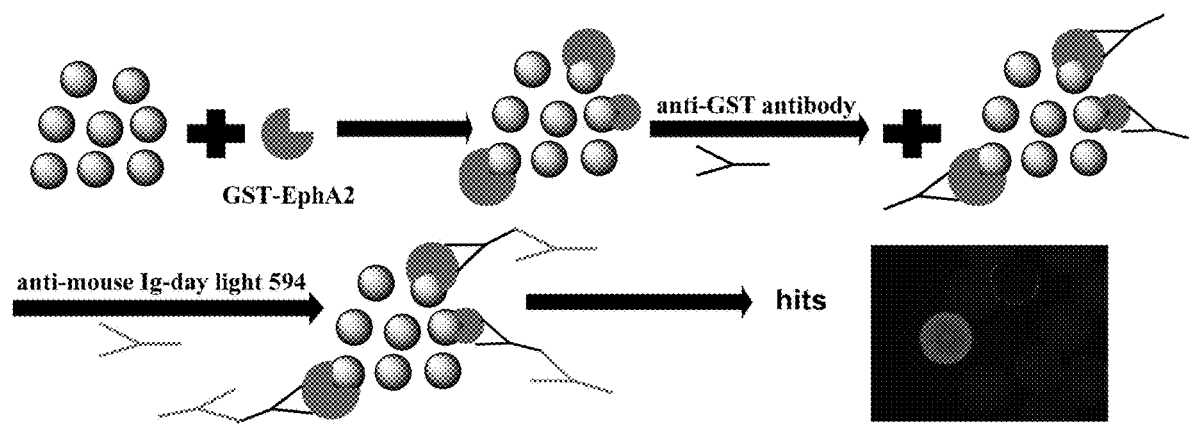
FIG. 12 shows a representative process for screening a γ-AApeptide library.

For example, in some embodiments, to conduct the library screening, the beads are incubated with GST tagged intracellular domain of EphA2 protein (FIG. 12). After wash and following incubation with the mouse anti-GST antibody, the beads are washed again and treated with the Alexa Flour 594 labeled goat-anti mouse secondary antibody. 12 red-colored beads were identified under the fluorescence microscope and picked up as the putative positive hits. Subsequently, these beads are incubated with guanidium chloride (GdmCl) to denature any potential proteins stuck on the surfaces of the beads. The coding peptides in the inner layers of the beads are then cleaved off the beads by treatment with the CNBr, and are sequenced by tandem MS/MS of MALDI.

In some embodiments, the structures of 7 peptides are determined unambiguously. Subsequently, the corresponding outer layer sequences of the 7 cyclic γ-AApeptides with fluorescein isothiocyanate (FITC) labels may be resynthesized and measured for their binding affinity toward EphA2 by fluorescence polarization (FP) assay. In some embodiments, the most potent hit exhibits excellent binding affinity to EphA2 with a $K_d$ value of 81 nM (FIG. 1). The potential binding to the GST tag was excluded as C-84 only showed negligible binding affinity to GST protein with a $K_d$ of 12.3 μM, which is ~150-fold weaker than that of EphA2 binding (FIG. 1).

Therapeutic Methods

The cyclic γ-AApeptide combinatorial library prepared according to the method disclosed herein may be used to identify of ligands to of a target protein of biological significance. In particular, a cyclic γ-AApeptide combinatorial library disclosed herein may be used to identify ligands to EphA2 (Ephrin type-A receptor 2), which plays prominent role in the pathogenesis of various tumors. EphA2 belongs to the family of Eph receptor tyrosine kinases which regulate tissue development, patterning of the visual system, and play a critical role in mediating the cell-cell communication and angiogenesis. Recent findings suggest that EphA2 overexpression is the key factor contributing to multiple cancers such as melanoma, ovarian, lung, and breast cancers. Therefore, the EphA2 is a promising target for cancer therapeutic development. Recently, considerable efforts have been exerted to the identification of inhibitors that block the capability of EphA2 for the phosphorylation of its downstream protein substrates, thereby dampening EphA2 mediated cell signaling. However, to date only limited success has been achieved. Thus, it is compelling to identify ligands from our macrocyclic γ-AApeptide library that bind to EphA2 with high affinity.

The advantage of the macrocyclic library disclosed herein is manifested by the identification of potent ligands that bind to EphA2 and modulate its biological activity. In particular, disclosed herein are macrocyclic γ-AApeptide compounds, such as compound C-84, which bind to the EphA2. With a $K_D$ value of 81 nM, the C-84 proves to be a potent inhibitor of the EphA2 signaling in both in vitro and cellular assay.

Figure 2A:
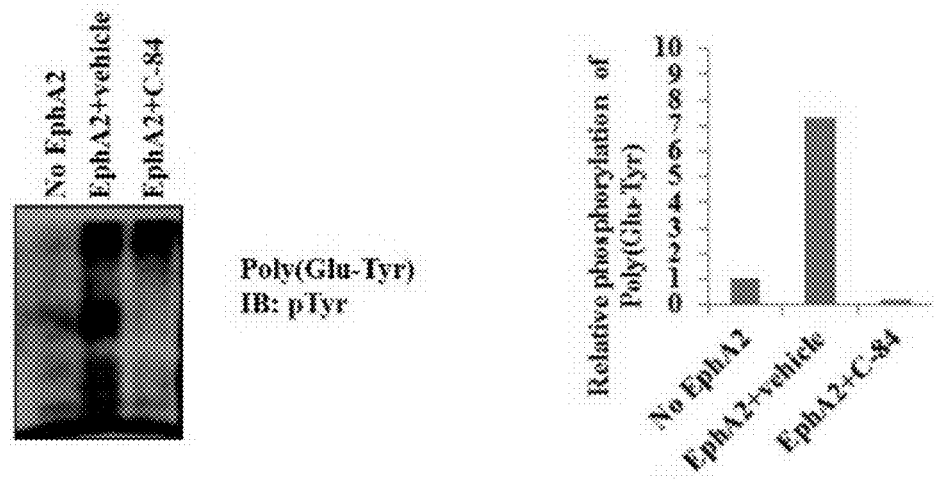
FIG. 2A, FIG. 2B, and FIG. 2C illustrate in-vitro inhibition of EphA2 by C-84 in vitro and in cellular assay.
Figure 2B:
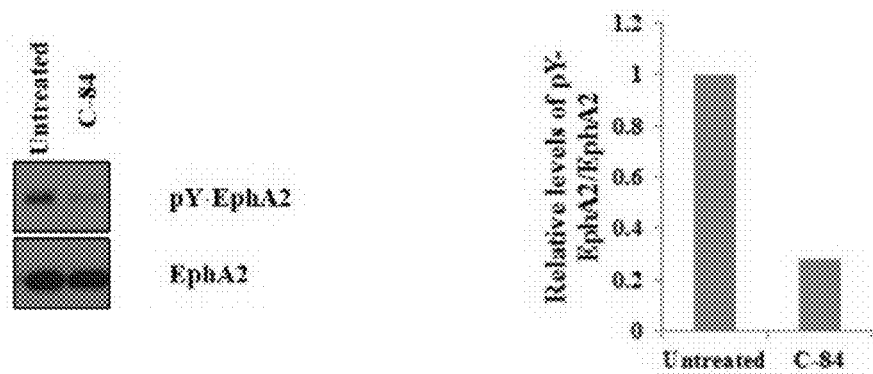
Figure 2C:
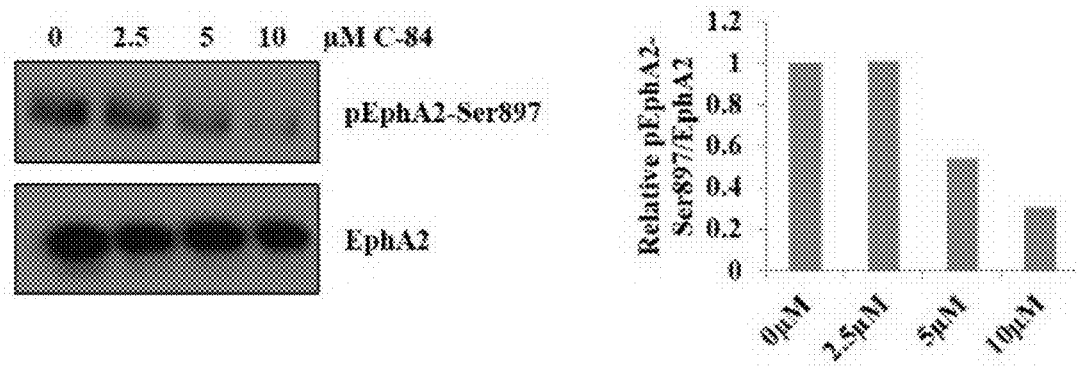

Given the strong binding affinity of C-84 toward EphA2, assays were performed to evaluate its biological activity. The initial in vitro kinase assay (FIG. 2A) show that 2 μM C-84 could completely inhibit EphA2 kinase activity by preventing phosphorylation of its substrate poly(Glu-Tyr). At the same concentration, C-84 also greatly suppressed the auto-catalytic activity of EphA2 (FIG. 2B). Both abovementioned in vitro kinase assays suggest C-84 is a potent inhibitor of EphA2 activity. C-84 was further tested for the regulation of catalytic activity in an ovarian cancer cell line C13 cells which displays high expression of EphA2. As shown in FIG. 2C, the phosphorylation level of EphA2 was inhibited on a dose-dependent fashion with the increased concentrations of C-84. The $IC_{50}$ of C-84 for the inhibition of EphA2 inhibition was approximately 5 μM (FIG. 2C).

Figure 3A:
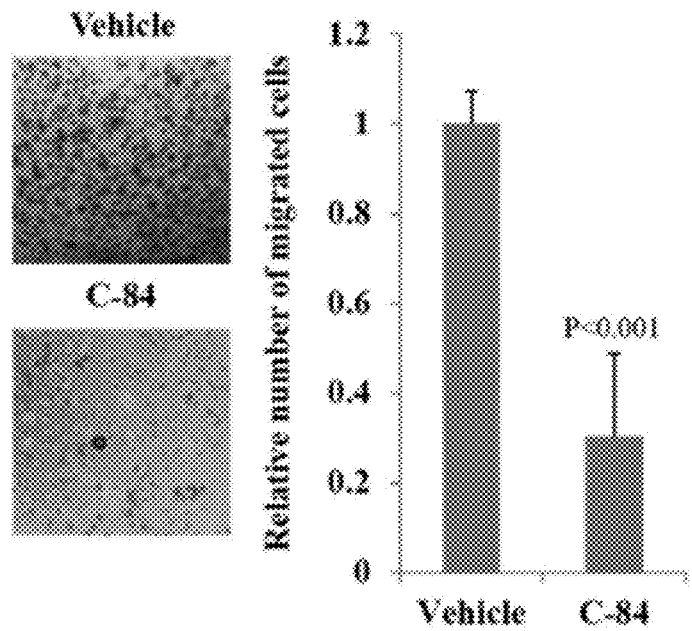
FIG. 3A and FIG. 3B illustrate the effects of C-84 on cell migration and invasion.
Figure 3B:
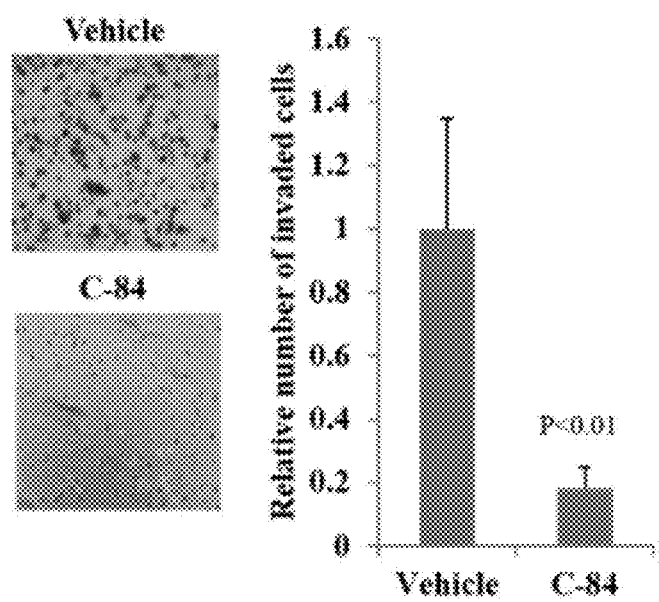
Figure 4:
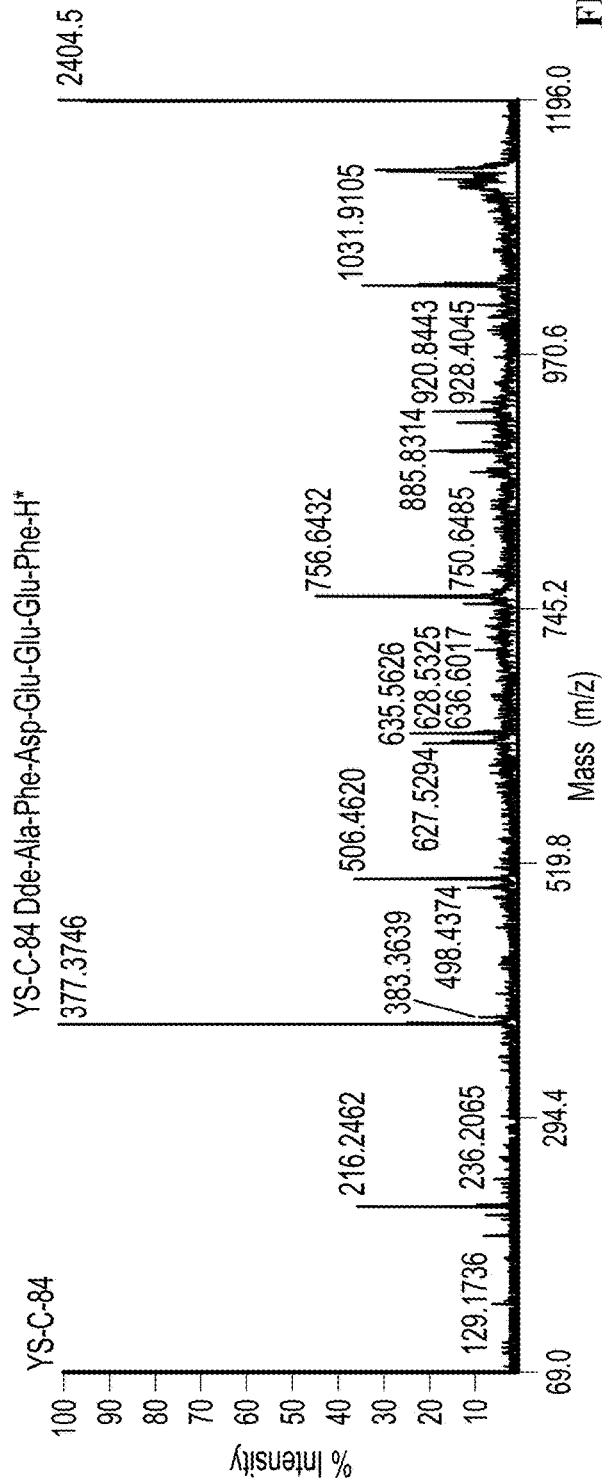
FIG. 4, FIG. 5, FIG. 6, FIG. 7, FIG. 8, FIG. 9, and FIG. 10 each illustrates the determination of the respective peptide decoding sequence, where H* stands for the homoserine lactone.
Figure 5:
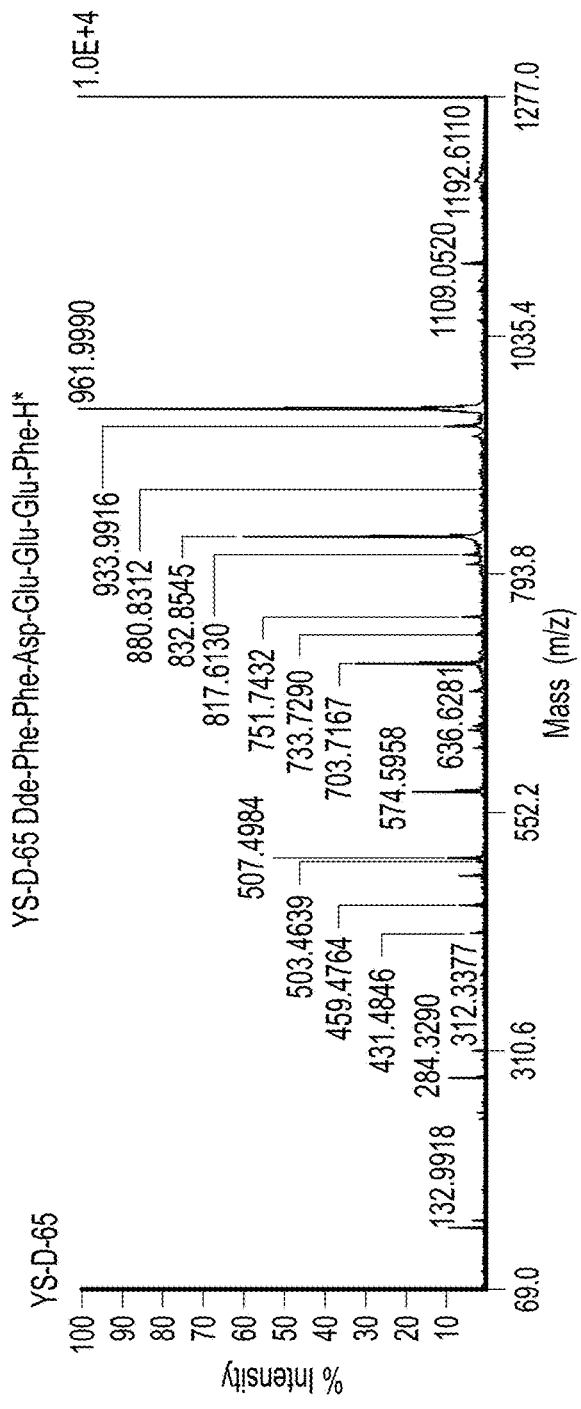
Figure 6:
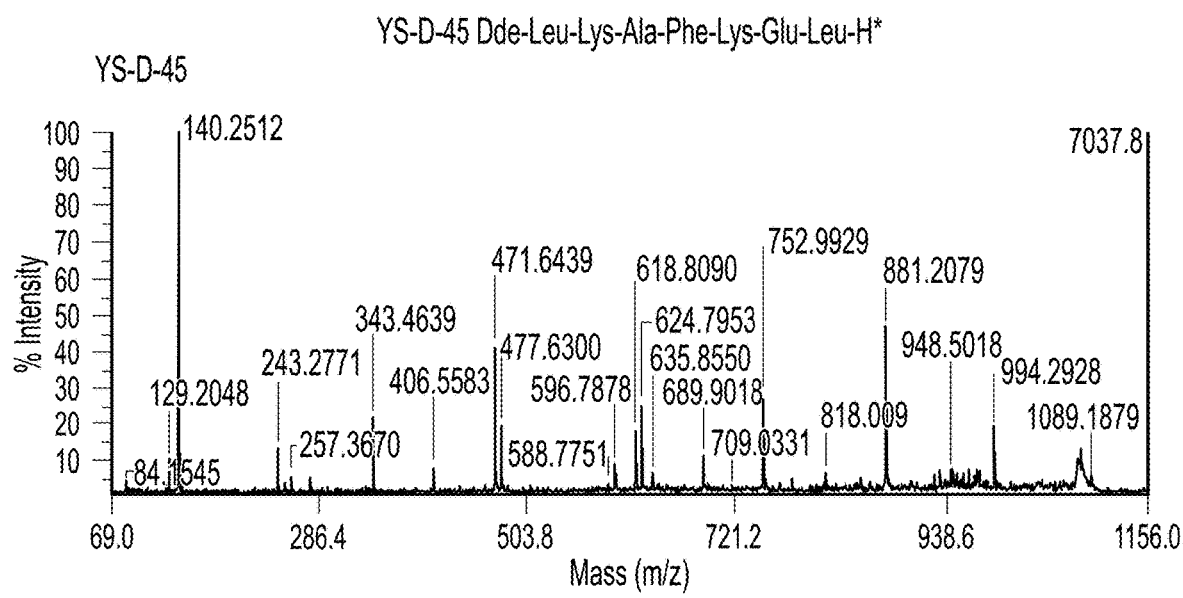
Figure 7:
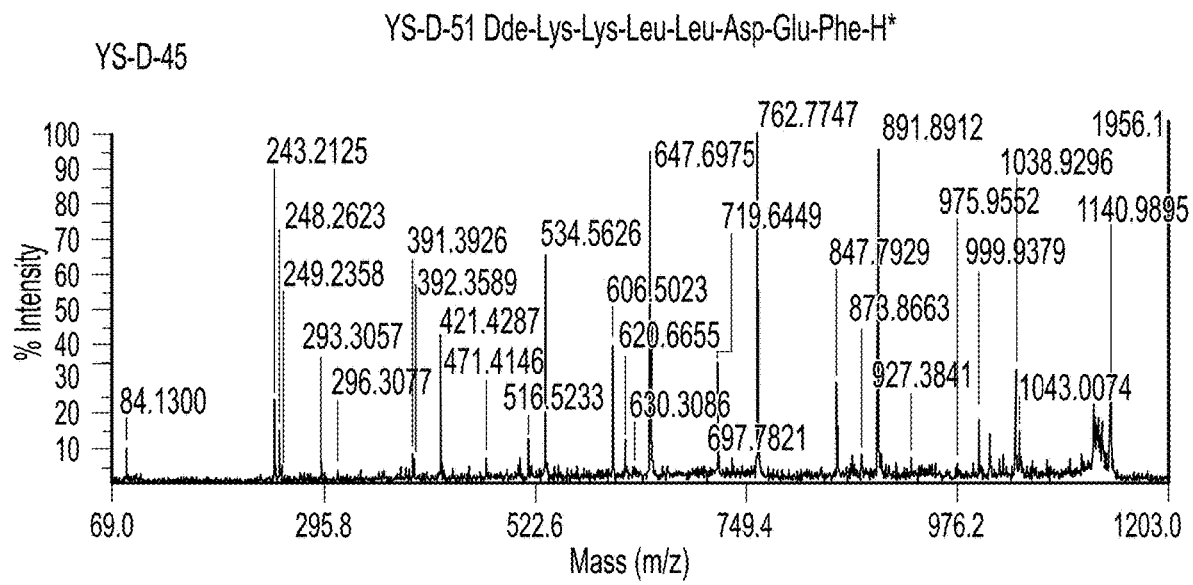
Figure 8:
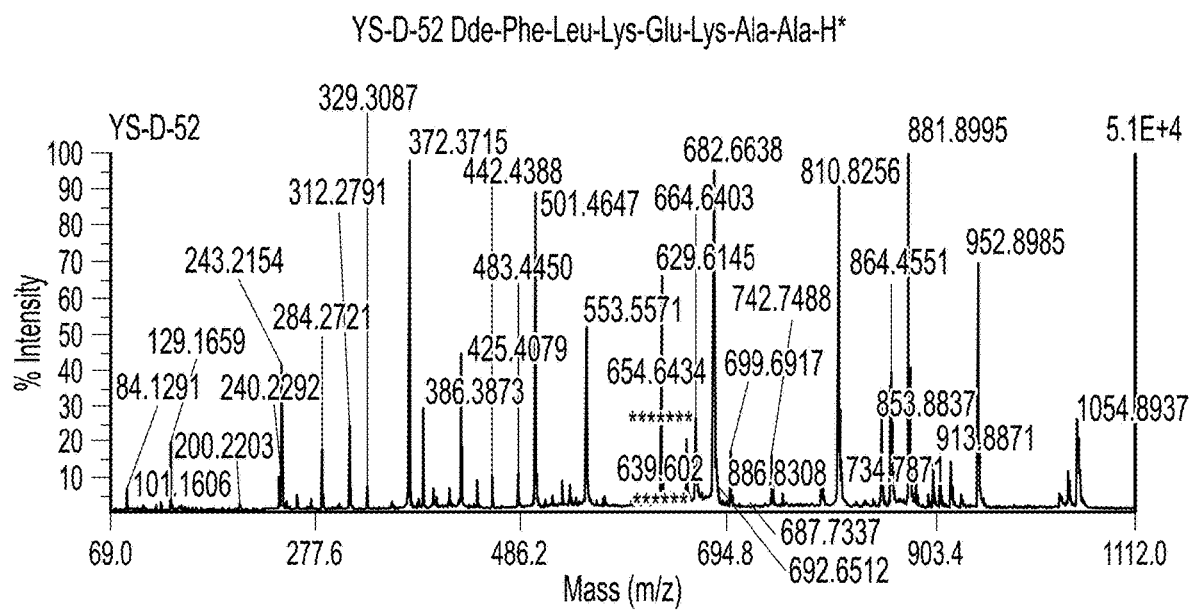
Figure 9:
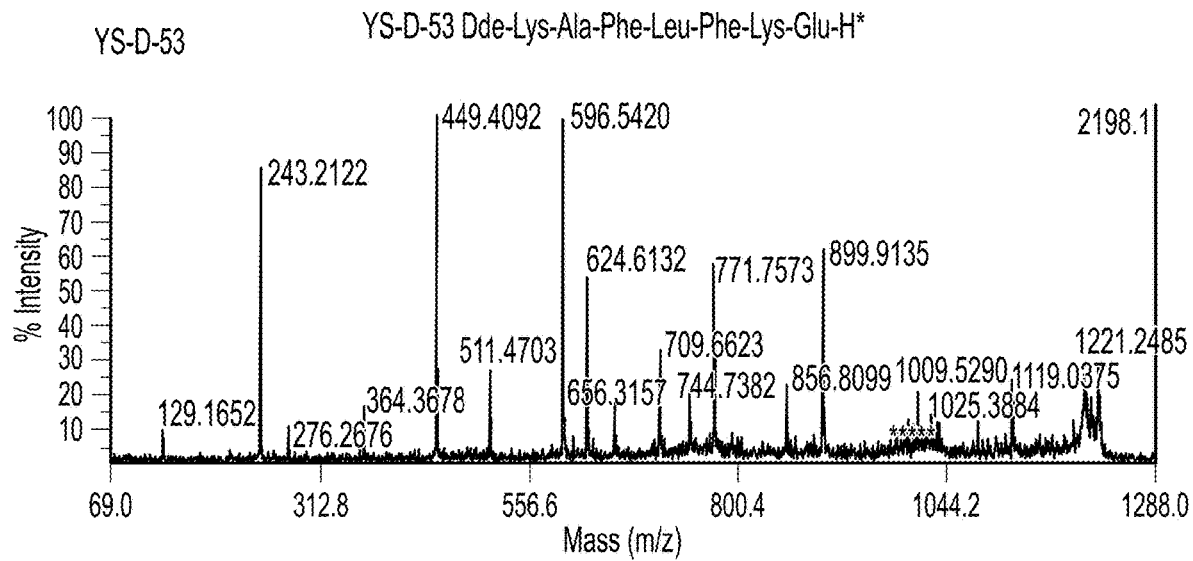
Figure 10:
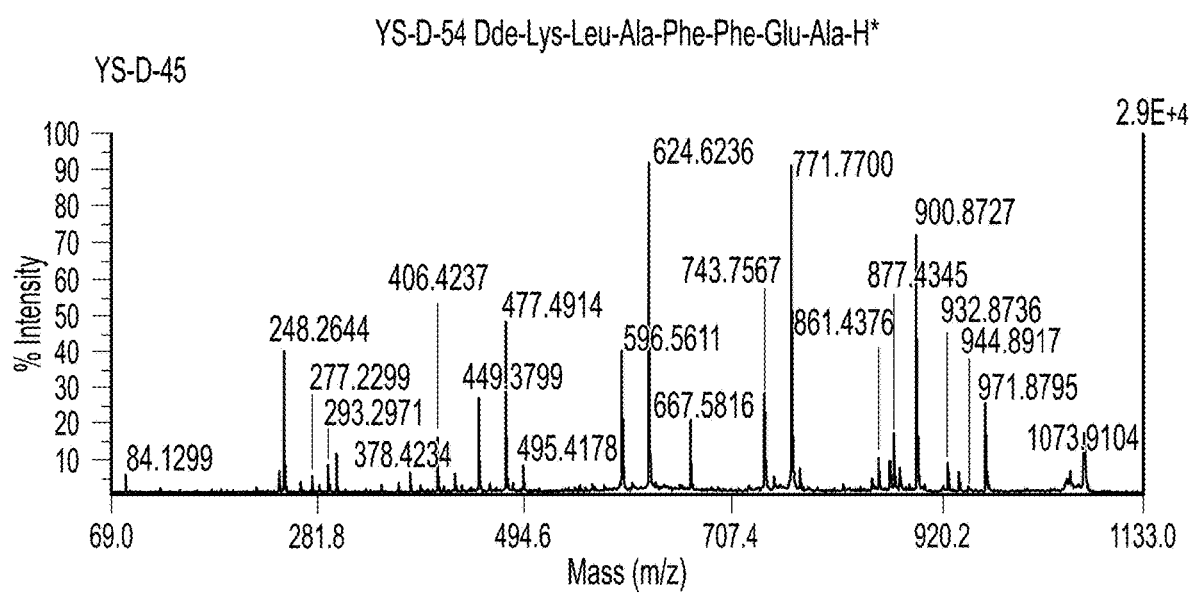

Since EphA2 was shown to play a critical role in cell migration, the effect of C-84 on cell migration and invasion was tested. Treatment of 10 μM C-84 led to around 70% and 80% decrease in cell migration (FIG. 3A) and invasion (FIG. 3B), respectively, suggesting EphA2 activity was significantly suppressed. Taken together, the ability of C-84 for the strong inhibition of EphA2 activity in cells suggests that cyclic γ-AApeptides possess excellent cell permeability, augmenting their future development in biomedical sciences.

In one aspect, provided is a method of inhibiting EphA2, which comprises administrating to a subject in need thereof a compound of disclosed herein, or pharmaceutically acceptable salts thereof, or a pharmaceutical composition thereof as described herein.

In some embodiments, the method of inhibiting EphA2 comprises administrating to a subject in need thereof a compound of formula (I), wherein G is H, or pharmaceutically acceptable salts thereof, or a pharmaceutical composition thereof as described herein. In some embodiments, the compound is C-84, having a structure of

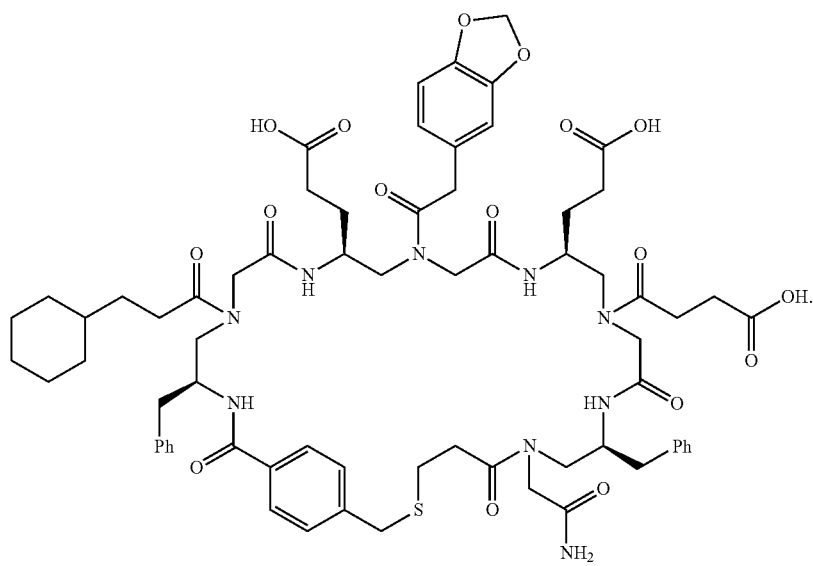 [SMILES: NC(=O)CN1C[C@H](Cc2ccccc2)NC(=O)CN(C(=O)CCC(=O)O)C[C@H](CCC(=O)O)NC(=O)CN(C(=O)Cc2ccc3c(c2)OCO3)C[C@H](CCC(=O)O)NC(=O)CN(C(=O)CCC2CCCCC2)C[C@H](Cc2ccccc2)NC(=O)c2ccc(cc2)CSCCC1=O]

In one aspect, provided is a method of treating a disease or disorder, such as cancer, which comprises administrating to a subject in need thereof a compound of disclosed herein, or pharmaceutically acceptable salts thereof, or a pharmaceutical composition thereof as described herein.

In some embodiments, the method of treating cancer comprises administrating to a subject in need thereof a compound of formula (I), wherein G is H, or pharmaceutically acceptable salts thereof, or a pharmaceutical composition thereof as described herein. In some embodiments, the compound is C-84.

In some embodiment, the compounds of disclosed herein, or pharmaceutically acceptable salts thereof, or pharmaceutical compositions thereof as described herein may be used to treat cancer, which is mediated by EphA2 or characterized by EphA2 overexpression. In some embodiments, the cancer is characterized by elevated level of EphA2-mediated cell signaling. In some embodiments, the cancer may be treated by reducing the level of EphA2-mediated cell signaling. In some embodiments, the cancer may be treated by reducing the level of EphA2 cellular expression. In some embodiment, the cancer is melanoma, ovarian cancer, lung cancer, or breast cancer.

Compounds of the present invention, or a pharmaceutically acceptable salt thereof, or pharmaceutical compositions thereof, can be administered to such subjects by a variety of methods. In any of the uses or methods described herein, administration can be by various routes known to those skilled in the art, including without limitation oral, intravenous, intramuscular, topical, subcutaneous, systemic, and/or intraperitoneal administration to a subject in need thereof.

The amount of the compound of the present invention, or a pharmaceutically acceptable salt thereof, required for use in treatment will vary not only with the particular compound or salt selected but also with the route of administration, the nature and/or symptoms of the cancer or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat a particular cancer.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to 4.0 mg/kg of body weight of the recipient per day. The compound may be administered in unit dosage form; for example, containing 1 to 500 mg, 10 to 100 mg or 5 to 50 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of the present invention, or pharmaceutically acceptable salts thereof, can be determined by comparing their in vitro activity, and in vivo activity in animal models. Such comparison can be done by comparison against an established drug for a particular type of cancer.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, FIPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the compound may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the cancer of interest will vary with the severity of the cancer to be treated and to the route of administration. The severity of cancer may be evaluated, in part, by standard prognostic evaluation methods. Further, the dose and dose frequency may also vary according to the age, body weight, and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

A therapeutically effective amount of a compound disclosed herein, or a pharmaceutically acceptable salt thereof, or a pharmaceutical composition as disclosed herein may be administered alone or in combination with a therapeutically effective amount of at least one additional anti-cancer therapeutic agents. In some embodiments, the compounds or pharmaceutical compositions as disclosed herein are administered in combination with at least one additional anti-cancer therapeutic agents. In some embodiments, the at least one additional anti-cancer therapeutic is administered prior to or following administration of the compounds or pharmaceutical compositions as disclosed herein.

5. Pharmaceutical Compositions

In another aspect of the invention, provided are pharmaceutical compositions, which comprises any of the compounds as described herein, or a pharmaceutically acceptable salt thereof, and a pharmaceutically acceptable carrier, adjuvant, or vehicle. In some embodiments, the pharmaceutical composition comprises a compound of formula (I), wherein G is H, or a pharmaceutically acceptable salt thereof, and a pharmaceutically acceptable carrier. In some embodiments, the pharmaceutical composition comprises compound C-84, or a pharmaceutically acceptable salt thereof, and a pharmaceutically acceptable carrier.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N(C_{1-4}alkyl)4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl (e.g., phenyl/substituted phenyl) sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the disease being treated.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, cement, putty, and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type may also be employed as fillers in soft and hardfilled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for rectal or vaginal administration are preferably suppositories which can be prepared by mixing the compounds disclosed herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Dosage forms for topical or trans dermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds described herein can be administered as a pharmaceutical composition comprising the compounds of interest in combination with one or more pharmaceutically acceptable carriers. It is understood, however, that the total daily dosage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health and prior medical history, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved. Actual dosage levels of active ingredients in the pharmaceutical compositions can be varied so as to obtain an amount of the active compound(s) that is effective to achieve the desired therapeutic response for a particular patient and a particular mode of administration. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer.

The compositions described herein may be administered with additional compositions to prolong stability, delivery, and/or activity of the compositions, or combined with additional therapeutic agents, or provided before or after the administration of additional therapeutic agents.

In certain embodiments, these compositions optionally further comprise one or more additional therapeutic agents, such as a therapeutic agents for treating cancer. Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

For adults, the doses are generally from about 0.01 to about 100 mg/kg, desirably about 0.1 to about 1 mg/kg body weight per day by inhalation, from about 0.01 to about 100 mg/kg, desirably 0.1 to 70 mg/kg, more desirably 0.5 to 10 mg/kg body weight per day by oral administration, and from about 0.01 to about 50 mg/kg, desirably 0.1 to 1 mg/kg body weight per day by intravenous administration.

The compositions and methods will be described more fully hereinafter with reference to the accompanying drawings, in which some, but not all embodiments of the invention are shown. Indeed, the invention may be embodied in many different forms and should not be construed as limited to the embodiments set forth herein. It is to be understood that the invention is not to be limited to the specific embodiments disclosed herein and that modifications and other embodiments are intended to be included within the scope of the invention.

6. Examples

Materials.

Fmoc-protected amino acids were purchased from Chemimpex (Wood Dale, Ill.). TentaGel resin (0.23 mmol/g) was purchased from RAPP Polymere (Tuebingen, Germany). Rink Amide-MBHA resin (0.55 mmol/g) was purchased from GL Biochem (Shanghai, China). 1-Hydroxybenzotriazole wetted with not less than 20% wt. water (HOBt), 1-Ethyl-3-(3-dimethylaminopropyl)carbodiimide (EDC), 5,5-Dimethyl-1,3-cyclohexanedione and 4,4'-Dimethoxytrityl Chloride were purchased from Oakwood Chemical (Estill, S.C.). 4-(Bromomethyl)benzoic acid was purchased from AK-Scientific (Union City, Calif.). 3-Mercaptopropionic Acid was purchased from TCI (Tokyo, Japan). Fluorescein isothiocyanate (FITC) was purchased from Chemodex (Gallen, Switzerland). Masses of γ-AApeptides and the MS/MS analysis were obtained on an Applied Biosystems 4700 Proteomics Analyzer. Solid phase synthesis was conducted in peptide synthesis vessels on a Burrell Wrist-Action shaker. γ-AApeptides were analyzed and purified on a Waters Breeze 2 HPLC system, and then lyophilized on a Labcono lyophilizer. Cell culture media was purchased from Gibco (Rockford, Ill.), fetal bovine serum (FBS) was purchased from Peak Serum (Fort Collins, Colo.), penicillinstreptomycin was purchased from Invitrogen (Carlsbad, Calif.). GST-EphA2 recombinant protein, Poly(Glu-Tyr) and Alexa Fluor 594 goat anti-mouse antibody were purchased from Life Technologies (Carlsbad, Calif.) and Sigma-Aldrich (St. Louis, Mo.) respectively. Phospho-Tyrosine HRP conjugated antibody (pTyr) was purchased from R&D Biosystems (Minneapolis, Minn.). pEphA2-Ser897 and EphA2 antibodies were purchased from Cell signaling technologies (Danvers, Mass.). Anti-GST antibody was purchased from Santa Cruz Biotechnology (Dallas, Tex.). All solvents and other chemical reagents were obtained from Sigma-Aldrich (St. Louis, Mo.) and were used without further purification.

Abbreviations

When used in the present application, the following abbreviations have the meaning set out below:
ACN is acetonitrile;
BSA/TBST is bovine serum albumin/tris-buffered saline, Tween
DCM is dichloromethane;
DCC is N,N'-dicyclohexylcarbodiimide;
Dde is (1-(4,4-dimethyl-2,6-dioxacyclohexylidene)ethyl)
DIC is N, N'-diisopropylcarbodiimide
DIPEA is diisopropylethylamine
DMF is N,N-dimethylformamide;
DMSO is dimethyl sulfoxide;
Dmt is 4,4'-Dimethoxytrityl
DMAP is 4-dimethylaminopyridine;
EDC/EDAC is N-(3-dimethylaminopropyl)-N'-ethylcarbodiimide hydrochloride;
EtOAc is ethyl acetate;
EtOH is ethanol;
FITC is fluorescein isothiocyanate;
HOBt is 1-hydroxybenzotriazole;
MeOH is methanol;
NEM is N-ethylmorpholine;
NMP is N-methylpyrrolidinone;
PyBop is (benzotriazol-1-yl-oxytripyrrolidinophosphonium hexafluorophosphate)
rt is room temperature; and
TFA is trifluoroacetic acid.

Synthesis
Synthesis of Cyclization Linker.
Synthesis of the Dmt Protected Mercaptopropionic Acid.

4,4'-Dimethoxytrityl Chloride (6.38 g, 18.82 mmol) was dissolved in 40 ml $CH_2Cl_2$ containing 3-Mercaptopropionic Acid (1.64 ml, 18.82 mmol) at room temperature. Triethylamine (3.93, 22.58 mmol) was slowly added to the above solution. The solution was stirred at room temperature for 4 hours to 6 hours. After that the mixture was evaporated under reduced pressure, the residue was washed by saturated citric acid and extracted by ethyl acetate (30 ml×3). The organic layer was dried over anhydrous $Na_2SO_4$ and evaporated. The product was purified by flashing column (Hexane: Ethyl acetate=1:1) to afford the desired product as a light yellow solid (80% yield). $^1$H NMR (500 MHz, $CDCl_3$): δ 7.42-7.44 (d, J=8.00 Hz, 2H), 7.34-7.35 (d, J=9.00 Hz, 2H), 7.29 (t, J=7.50 Hz, 2H), 7.21 (t, J=7.50 Hz, 1H), 6.84-6.82 (d, J=9.00 Hz, 2H), 3.79 (s, 6H), 2.49 (t, J=7.50 Hz, 2H), 2.30 (t, J=7.50 Hz, 2H); $^{13}$C NMR (125 MHz, $CDCl_3$): δ 178.2, 158.1, 145.2, 137.0, 130.7, 129.4, 127.9, 126.6, 113.2, 66.0, 55.2, 33.5, 26.6.

Synthesis of the 4-(Bromomethyl)Benzoyl Chloride

The 4-(bromomethyl) benzoic acid (5 g, 23.25 mmol) was dissolved in 10 ml thionyl chloride and reflux for 5 hours. The excess thionyl chloride was removed under reduced pressure to afford the desired product as a white solid (85% yield). $^1$H NMR (500 MHz, $CDCl_3$): δ 8.06 (d, J=5.00 Hz, 2H), 7.52 (d, J=10.00 Hz, 2H), 4.50 (s, 2H); $^{13}$C NMR (125 MHz, $CDCl_3$): δ 167.7, 145.3, 132.9, 131.8, 31.4.

Synthesis of 2-acetyl-5,5-dimethylcyclohexane-1,3-dione

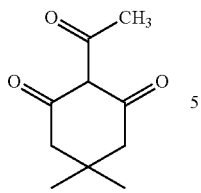

To a 100-mL flask was added with 5,5-dimethylcyclohexane-1,3-dione (10 g, 71.34 mmol), N, N-Diisopropylethylamine (14.91 ml, 85.6 mmol), 4-Dimethylaminopyridine (435.76 mg, 3.57 mmol) and DCM 50 ml. The mixture was stirred in an ice bath to which acetyl chloride (6.08 mL, 85.6 mmol) was added. The reaction was warmed up to room temperature and allowed to stir for 8 hours. The solvent was evaporated and the residue was washed with 1M HCl then extracted with ethyl acetate (30 ml×3). The organic layer was dried over anhydrous $Na_2SO_4$ and then removed in vacuo. The residue was purified by flash column (Hexane: Ethyl acetate=1:1) to afford the 2-acetyl-5,5-dimethylcyclohexane-1,3-dione as a yellowish solid (11 g, yield 85%). $^1$H NMR (500 MHz, $CDCl_3$): δ 2.54 (s, 3H), 2.48 (s, 3H), 2.3 (s, 2H), 1.01 (s, 6H); $^{13}$C NMR (125 MHz, $CDCl_3$): δ 202.3, 197.8, 195.1, 112.3, 52.4, 46.8, 30.6.

Synthesis of Dde Protected Amino Acids.

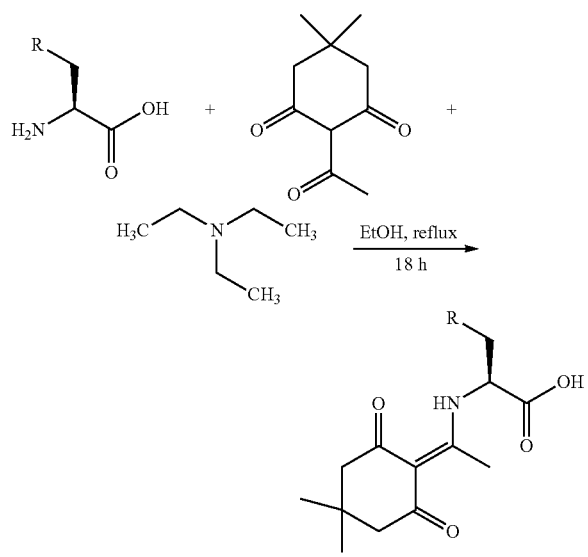

L-Amino acid (1 equiv) was suspended in a solution of the 2-acetyl-5,5-dimethylcyclohexane-1,3-dione (1.3 equiv) in absolute ethanol (ca. 50 mL). Triethylamine (1.5 equiv) was added and the reaction mixture was refluxed for 18 hours. The resulted yellow solution was cooled and concentrated under reduced pressure. The residue was dissolved in $CH_2Cl_2$ (ca. 50 mL), washed twice with aqueous 1 M HCl (ca. 50 mL), dried over $Na_2SO_4$, filtered and concentrated in vacuo. $Et_2O$ (ca. 40 mL) resulted in immediate white precipitate, which was filtered and washed with cold $Et_2O$ to afford the title compound as an off-white crystalline solid (~70%).

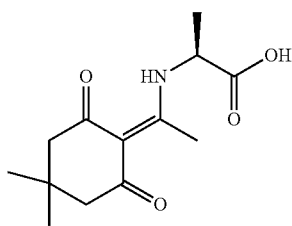 [SMILES: CC(N[C@@H](C)C(=O)O)=C1C(=O)CC(C)(C)CC1=O]

Dde-Ala-OH. white solid. $^1$H NMR (500 MHz, DMSO-d6): δ 13.51 (s, 1H), 4.61 (t, J=5.00 Hz, 1H), 2.48 (s, 3H), 2.27 (s, 4H), 1.41 (d, J=5.00 Hz, 3H), 0.92 (s, 6H); $^{13}$C NMR (125 MHz, $CDCl_3$): δ 197.4, 172.9, 172.5, 107.6, 52.8, 51.6, 30.3, 28.3, 19.1, 18.1. HRMS (ESI) ([M+H]$^+$) Calcd. for $C_{13}H_{20}NO_4$: 254.1392, found:

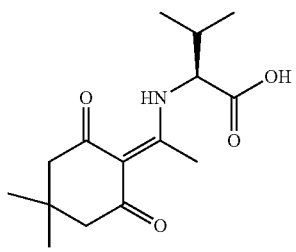 [SMILES: CC(N[C@H](C(=O)O)C(C)C)=C1C(=O)CC(C)(C)CC1=O]

Dde-Val-OH. white solid. $^1$H NMR (500 MHz, $CDCl_3$): δ 13.6 (s, 1H), 4.61 (t, J=5.00 Hz, 1H), 2.5 (s, 3H), 2.39 (s, 4H), 2.36 (m, 1H), 1.08 (d, J=5.00 Hz, 3H), 1.04 (d, J=5.00 Hz, 3H), 1.0 (s, 6H); $^{13}$C NMR (125 MHz, $CDCl_3$): δ 174.3, 171.6, 107.9, 62.3, 51.9, 31.1, 30.1, 28.1, 19.1, 18.7, 17.0.

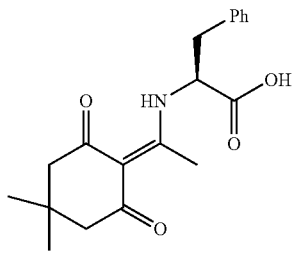 [SMILES: CC(N[C@@H](Cc1ccccc1)C(=O)O)=C1C(=O)CC(C)(C)CC1=O]

Dde-Phe-OH. white solid. $^1$H NMR (500 MHz, $CDCl_3$): δ 13.71 (s, 1H), 7.18-7.27 (m, 5H), 4.57-4.61 (m, 1H), 3.05-3.09 (m, 2H), 2.36 (s, 4H), 2.20 (s, 3H), 1.00 (s, 6H); $^{13}$C NMR (125 MHz, $CDCl_3$): δ 198.1, 173.6, 171.0, 135.5, 129.4, 128.6, 127.4, 107.9, 58.3, 52.4, 45.5, 39.3, 30.1, 28.0, 18.1, 8.5.

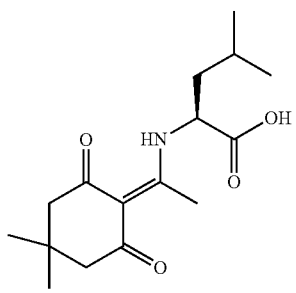 [SMILES: CC(N[C@@H](CC(C)C)C(=O)O)=C1C(=O)CC(C)(C)CC1=O]

Dde-Leu-OH. white solid. $^1$H NMR (500 MHz, CDCl$_3$): δ 13.60 (s, 1H), 4.57-4.61 (m, 1H), 2.50 (s, 3H), 2.37 (s, 4H), 1.82 (m, 2H), 1.77 (m, 1H), 0.99 (s, 6H), 0.95 (d, J=5.00 Hz, 3H), 0.89 (d, J=5.00 Hz, 3H); $^{13}$C NMR (125 MHz, CDCl$_3$): δ 198.9, 173.9, 107.9, 54.9, 52.3, 45.6, 41.3, 30.1, 28.2, 24.8, 22.7, 21.7, 18.7, 8.4.

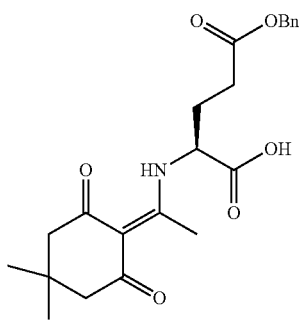 [SMILES: CC(N[C@@H](CCC(=O)OCc1ccccc1)C(=O)O)=C1C(=O)CC(C)(C)CC1=O]

Dde-Glu(OBn)-OH. pale yellow solid. $^1$H NMR (500 MHz, DMSO-d6): δ 13.77 (s, 1H), 7.33 (s, 5H), 5.10 (s, 2H), 4.55 (m, 1H), 2.53-2.59 (m, 2H), 2.51 (s, 3H), 2.39 (s, 4H), 2.21-2.25 (m, 2H), 1.01 (s, 6H); $^{13}$C NMR (125 MHz, CDCl$_3$): δ 174.3, 171.9, 171.2, 135.4, 128.6, 128.4, 128.3, 128.2, 66.7, 55.4, 52.3, 30.2, 29.6, 28.2, 27.7, 18.7.

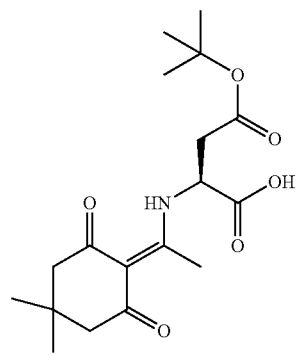 [SMILES: CC(N[C@@H](CC(=O)OC(C)(C)C)C(=O)O)=C1C(=O)CC(C)(C)CC1=O]

Dde-Asp-OH. white solid. $^1$H NMR (500 MHz, DMSO-d6): δ 13.56 (s, 1H), 4.84 (m, 1H), 2.90 (dd, J=15.00, 5.00 Hz, 1H), 2.78 (dd, J=15.00, 5.00 Hz, 1H), 2.46 (s, 3H), 2.27 (s, 4H), 1.36 (s, 9H), 0.92 (s, 6H); $^{13}$C NMR (125 MHz, CDCl$_3$): δ 172.3, 170.7, 168.7, 107.7, 81.5, 52.5, 38.2, 30.1, 38.3, 28.0, 17.9.

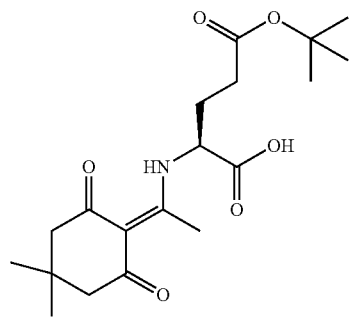 [SMILES: CC(N[C@@H](CCC(=O)OC(C)(C)C)C(=O)O)=C1C(=O)CC(C)(C)CC1=O]

Dde-Glu-OH. white solid. $^1$H NMR (500 MHz, DMSO-d6): δ 13.54 (s, 1H), 4.26 (q, J=5.00 Hz, 1H), 2.43 (s, 3H), 2.28 (s, 4H), 2.24-2.26 (m, 2H), 1.90-2.10 (m, 2H), 1.36 (s, 9H), 0.93 (s, 6H); $^{13}$C NMR (125 MHz, CDCl$_3$): δ 172.7, 171.8, 107.4, 80.3, 54.2, 52.1, 45.2, 30.8, 30.1, 28.3, 28.1, 27.8.

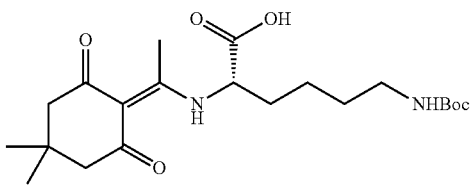 [SMILES: CC(N[C@@H](CCCCNC(=O)OC(C)(C)C)C(=O)O)=C1C(=O)CC(C)(C)CC1=O]

Dde-Lys-OH. white solid. H NMR (500 MHz, CDCl$_3$): δ 13.69 (s, 1H), 4.80 (m, 1H), 4.40 (m, 2H), 3.09 (m, 2H), 2.50 (s, 3H), 2.34 (s, 4H), 1.95 (m, 2H), 1.50 (m, 2H), 1.40 (s, 9H), 1.01 (s, 6H); $^{13}$C NMR (125 MHz, CDCl$_3$): δ 173.3, 172.9, 172.0, 171.6, 155.9, 107.6, 80.9, 78.9, 60.1, 56.1, 40.9, 39.8, 32.1, 30.3, 29.1, 27.9, 21.6, 18.4, 13.9.

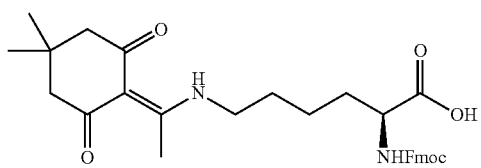

Fmoc-Lys(Dde)-OH. pale yellow solid. $^1$H NMR (500 MHz, CDCl$_3$): δ 13.29 (s, 1H), 7.73-7.74 (d, J=5.00 Hz, 2H), 7.58 (t, J=5.00 Hz, 2H), 7.37 (t, J=5.00 Hz, 2H), 7.27 (t, J=5.00 Hz, 2H), 5.79 (d, J=10.00 Hz, 1H), 4.42-4.46 (m, 1H), 4.35-4.37 (d, J=10.00 Hz, 2H), 4.18 (t, J=5.00 Hz, 1H), 3.38-3.39 (m, 2H), 2.53 (s, 3H), 2.35 (s, 4H), 1.78-1.80 (m, 2H), 1.70-1.72 (m, 2H), 1.47-1.57 (m, 2H), 1.00 (s, 6H); $^{13}$C NMR (125 MHz, CDCl$_3$): δ 198.5, 174.7, 174.3, 156.2, 143.8, 143.7, 141.3, 127.7, 127.0, 125.1, 119.9, 107.8, 67.1, 53.4, 52.2, 47.1, 43.4, 31.9, 30.2, 28.3, 28.2, 22.4, 21.1, 18.3, 14.2.

One-Bead Two-Compounds Library Preparation.

The One-bead Two-compounds cyclic γ-AApeptide library was prepared on TentaGel NH$_2$ resin (2.64 g, 0.61 mmol, 405000 beads) using split and pool method at room temperature. Theoretically each bead of the library contained two layers, with inner layer being a coding peptide and outer layer as the cyclic γ-AApeptide ligand. Unless otherwise noted, in the outer layer, the Fmoc protecting group was removed by 20% (v/v) piperidine in DMF (10 min×2). The Alloc protecting group was removed by Pd(PPh$_3$)$_4$ (8 mg, 0.007 mmol) and Me$_2$NH.BH$_3$ (25 mg, 0.42 mmol) in 3 mL DCM (10 min×2). All the Alloc protected γ-AApeptide building blocks (2 equiv) and carboxylic acids (2 equiv) were coupled to desired amino groups on the solid phase using HOBt/DIC (4:4 equiv.) as the coupling reagents in DMF for 6 hours twice. All the acyl chlorides (2 equiv.) were coupled to desired amino groups in DCM containing DIPEA (4 equiv.) for 30 minutes twice. In the inner layer of the beads, the Dde protected amino acids (5.5 equiv.) were coupled to the desired amino groups in DMF for 3 hours in the presence of PyBop (5 equiv.) and NEM (11 equiv.). Dde deprotection solution was prepared by suspending 1.25 g (0.180 mmol) of NH$_2$OH.HCl and 0.918 g (0.135 mmol) of imidazole in 5 mL NMP, and the mixture was sonicated until complete dissolution. The deprotection solution was added 1 mL CH$_2$Cl$_2$ before use.

The formation of bi-layers on the beads was achieved following previously reported protocols (Scheme 3, Table 1). Briefly, the resin was soaked in water overnight. After being transferred into the peptide reaction vessel, the resin was quickly drained and washed with 1:1 (v/v) DCM/diethyl ether. A solution of (Boc)$_2$O (0.5 equiv.) in 1:1 (v/v) DCM/diethyl ether was added, and the mixture was shaken on the Burrell Wrist-Action shaker for 3 hours, followed by the wash with DCM (3×) and DMF (3×). Next, Fmoc-Met-OH (0.5 equiv.), HOBt (2 equiv.) and DIC (2 equiv.) were added to react with the inner layer of the resin. The Fmoc group was removed and the beads were split into 5 portions, which were reacted with the Dde-Ala-OH, Dde-Phe-OH, Dde-Leu-OH, Dde-Val-OH, and Dde-Glu(OBn)-OH in 5 peptide synthesis vessels, respectively. Subsequently, the Boc protecting group on the outer layer was removed by using 94% TFA, 2% TIS (triisopropylsilane), 2% H$_2$O and 2% Thioanisole, and the exposed amine was coupled with the corresponding γ-AApeptide building blocks. Following that, the Alloc protecting group on the γ-AApeptide building blocks were removed, and the Dmt protected mercaptopropionic acid was added to react with the secondary amine. Next, all the beads were pooled and mixed thoroughly and then split into 5 portions. The Dde of the coding peptide in the inner layer was removed and 5 Dde protected amino acids as the previous step. Then the Fmoc group of the γ-AApeptide in the outer layer was removed and the sequence was coupled with desired γ-AApeptide building blocks. Then the beads were pooled and split again, and the synthetic cycle was repeated three more times. The last Dde protecting group was left on the decoding layer, while the Fmoc group of the incubate layer was removed then coupled with the 4-(bromomethyl)benzoyl chloride. Following that, the Dmt protecting group was removed by 2% TFA, 2% triisopropylsilane and 96% CH$_2$Cl$_2$ for 2 minutes (×5) until the deprotecting solution became colorless. The cyclization of γ-AApeptide was achieved by adding the solution of (NH$_4$)$_2$CO$_3$ (10 equiv) in 1:1 (v/v) DMF/H$_2$O to the resin and shaking the mixture for 8 hours. The resin was washed with DMF (3×) and DCM (3×). Finally, protecting groups on the sidechains were removed with 94% TFA, 2% triisopropylsilane, 2% H$_2$O and 2% Thioanisole for 1 hour.

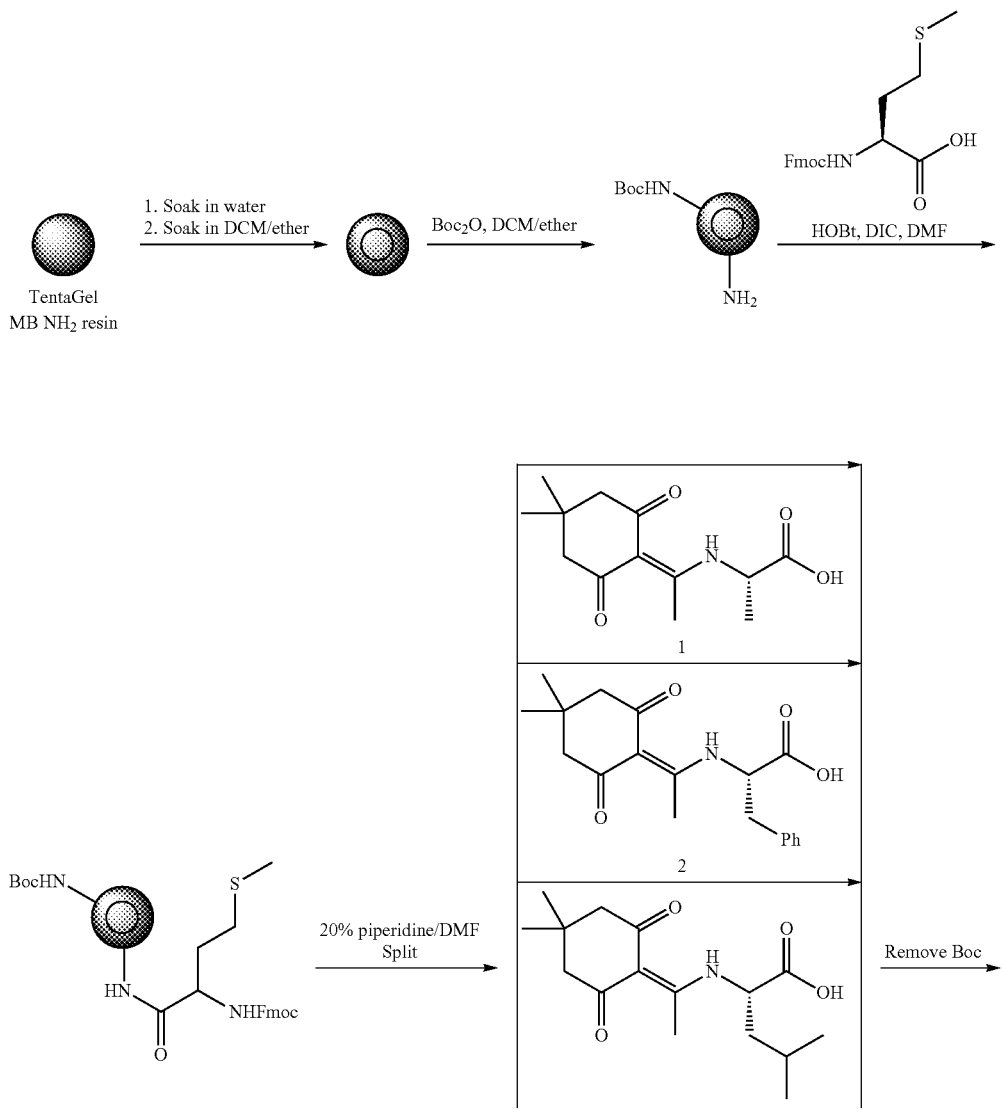

Scheme 3. The Preparation of the S-mediated cyclic library.

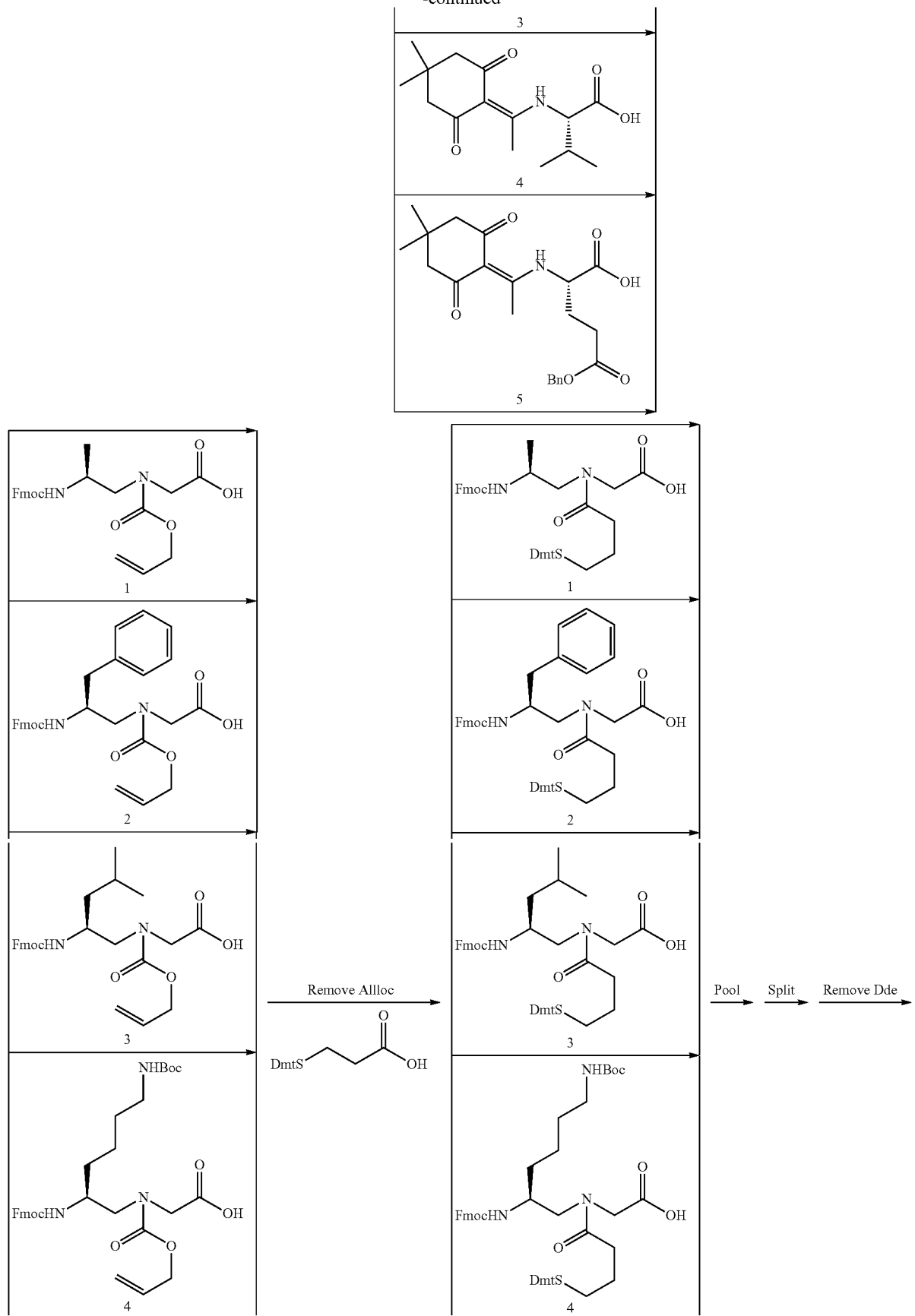

-continued
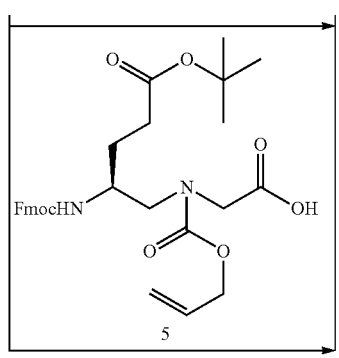
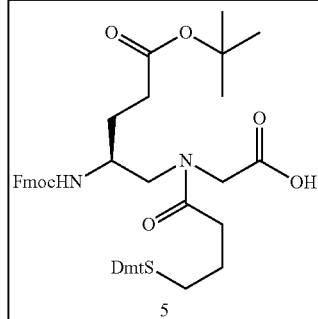
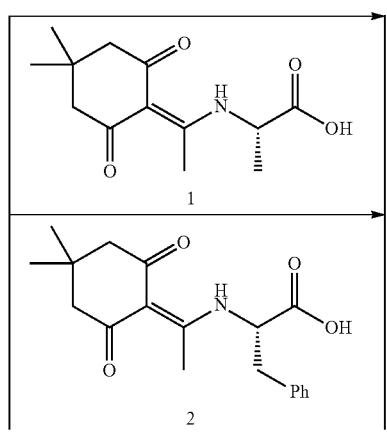
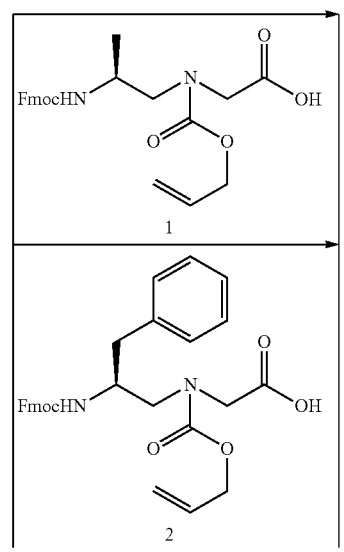
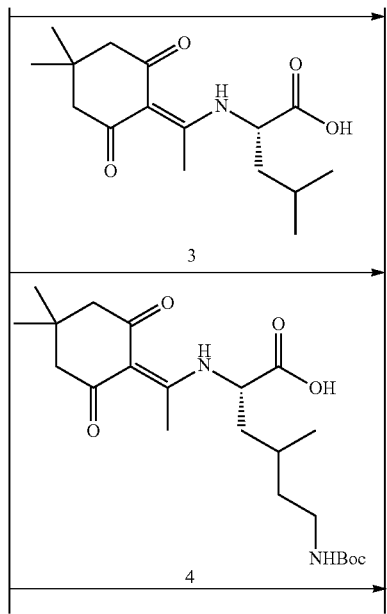
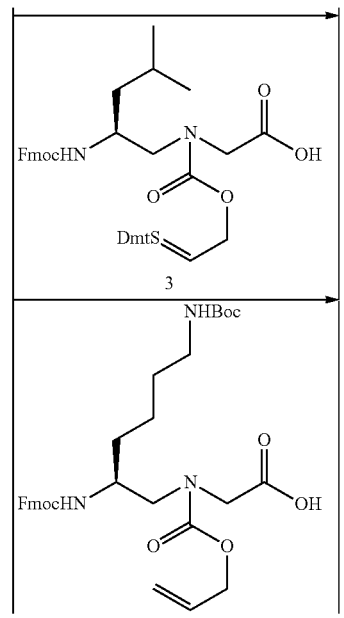

-continued
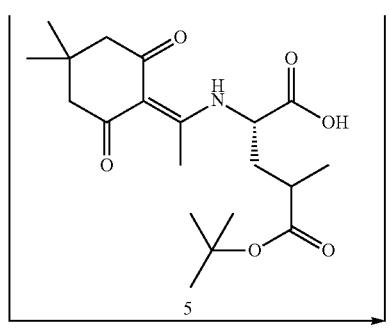
5
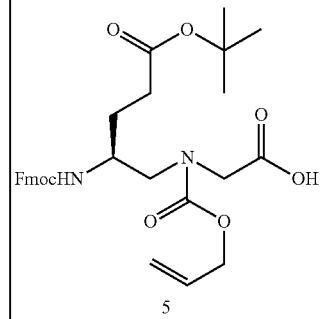
4
5
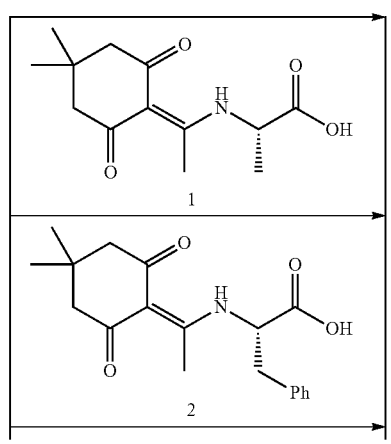
1
2
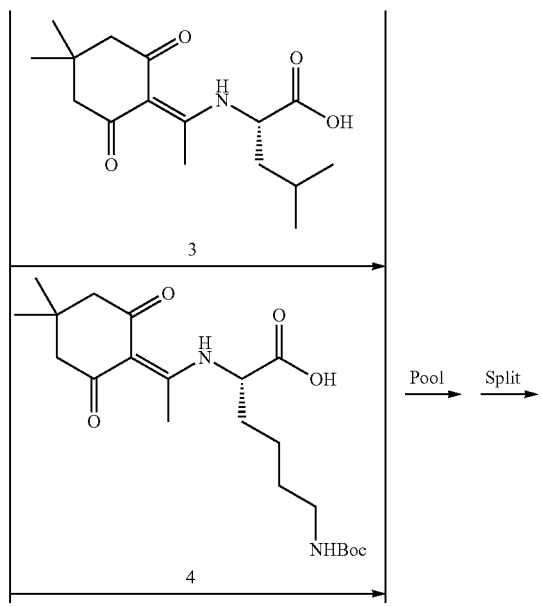
3
4
Pool → Split →

-continued
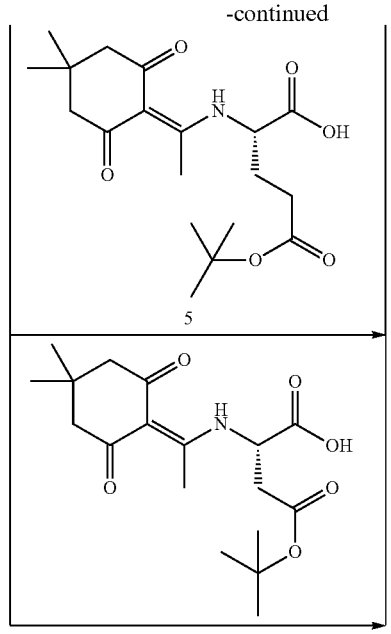
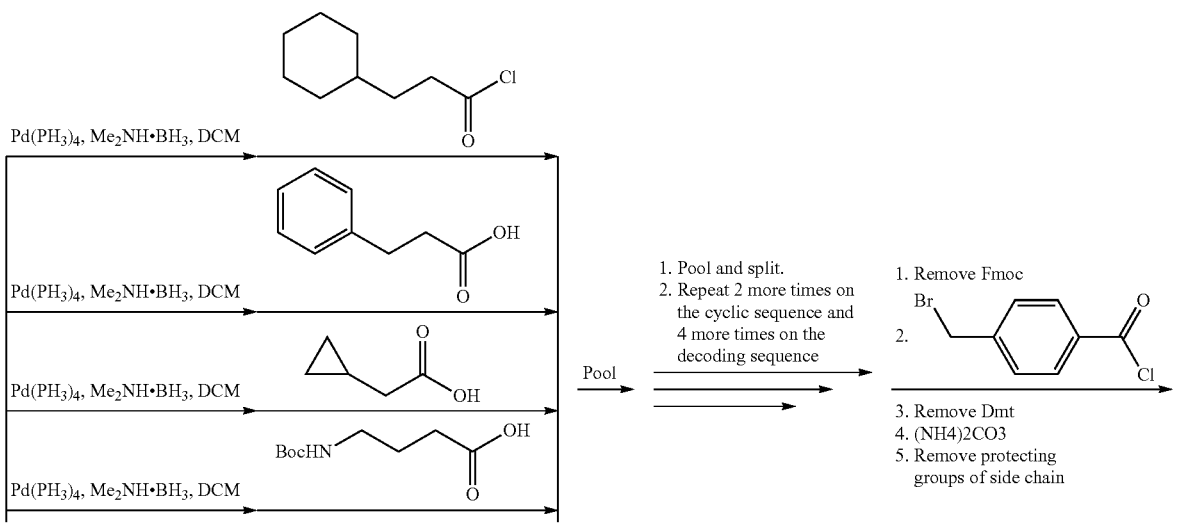
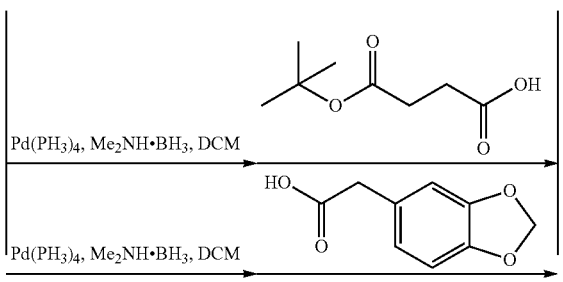

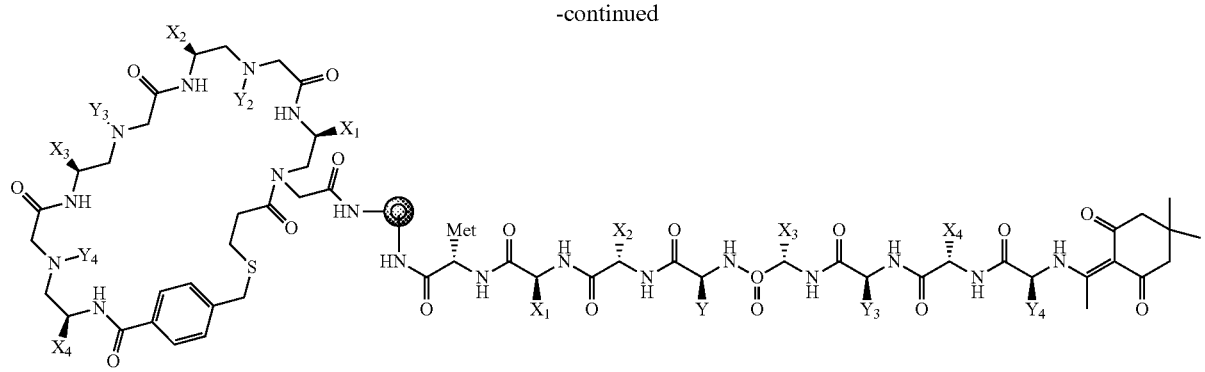
Library Diversity
5x5x6x5x6x5x6 = 135000
-continued

TABLE 1

Encoding map.

TABLE 1-continued

Encoding map.

$X_2 = X_3 = X_4$ (Encoding Layer)

$Y_2 = Y_3 = Y_4$ (Outer Layer)

$Y_2 = Y_3 = Y_4$ (Encoding Layer)

Library Screening.

General Information

The EphA2-GST protein was used as a target for the combinatorial library screening. The beads were screened and picked up under a Zeiss inverted fluorescence microscope installed with a 10×43HE filter. To avoid any possible nonspecific binding, EphA2 and antibodies solution were all made in 1% BSA/TBST blocking buffer.

Beads Screening

The TentaGel beads (2.64 g, 405000 beads, 135000 compounds) were swelled in DMF for 1 hour. After being washed with Tris buffer for five times, the beads were equilibrated in Tris buffer overnight at room temperature, followed by incubation with the blocking buffer (1% BSA in Tris buffer with a 1000× excess of cleared E. coli lysate) for 1 hour.

Prescreening: The blocked beads were incubated with the mouse anti-GST antibody (1:1000 dilution) for 2 hours at room temperature. After thorough wash with 1×Tris buffer, the beads were then incubated with the goat anti-mouse IgG conjugated with Alexa Fluor daylight 594 (1:1000 dilution) for 2 hours at room temperature. The beads were washed with the Tris buffer (3×), and then transferred into a 6-well plate to be observed under Zeiss inverted fluorescence microscope installed with the 10×43HE filter. The beads emitting red fluorescence were picked up and excluded from formal screening.

The rest of the beads were pooled together into the peptide vessel, washed with Tris buffer, and then treated with 8 M guanidine-HCl at room temperature for 1 hour to remove any bound proteins. The guanidine-HCl was washed away by both water (10×) and Tris buffer (5×). The beads were washed and incubated in DMF for 1 hour, followed by washing and equilibration in Tris buffer overnight.

Screening: The beads were incubated in 1% BSA/Tris buffer and 1000× excess of E. coli lysate for 1 hour at room temperature. After wash with Tris buffer for 5 times, the beads were incubated with EphA2-GST protein at a concentration of 50 nM for 4 hours at room temperature with a 1000× excess of E. coli lysate. After thorough wash with Tris buffer, the library beads were incubated in 10 mL mouse anti-GST antibody for 2 hours at room temperature. The beads were washed by Tris buffer for 5 times with caution and incubated with goat anti-mouse IgG conjugated with Alexa Fluor daylight 594 for 1 hour at room temperature. The beads were washed and then transferred into the 6-well plate with Tris buffer, and observed under the Zeiss inverted fluorescence microscope. The beads emitting read fluorescence were picked up as putative hits for further validation. Each hit was transferred to an Eppendorf microtube, and denatured in 100 μL 8M guanidine-HCl for 1 hour at room temperature, respectively. The bead was rinsed with Tris buffer 3×10 minutes, water 3×10 minutes, 50/50 DMF/H$_2$O 3×10 minutes, DMF 3×10 minutes, and ACN 3×10 minutes. At last the resin was placed in ACN overnight in each microtube and then ACN was evaporated. The bead was incubated in the cocktail of 5:4:1 (v:v:v) of ACN:glacial acetic acid:H$_2$O containing cyanogen bromide (CnBr) at a concentration of 50 mg/mL overnight at room temperature. The cleavage solution was then evaporated, and the cleaved peptide was dissolved in ACN:H$_2$O (4:1) and subject to MALDI TOF-TOF analysis.

Synthesis of the (FITC) Hits.

After structures of putative hits were determined by MALDI MS/MS, the FITC labeled hits were re-synthesized on the Rink Amide resin and confirmed by Applied Biosystems 4700 Proteomics Analyzer (Table 2). Briefly, the Fmoc-Lys(Dde)-OH was first attached to the Rink amide resin. The Fmoc protection group was then removed, followed by the desired building blocks needed for the sequence synthesis. After the γ-AApeptides were cyclized, the Dde group was removed. Then FITC (2 equiv.) and DIPEA (6 equiv.) in DMF were added to the resin and shaken for 12 hours at room temperature. The FITC labeled cyclic γ-peptide was cleaved by 1:1 (v/v) DCM/TFA containing 2% triisopropylsilane. The crude was purified by the Waters HPLC system with flow rate of 0.8 mL/min with a linear gradient from 5% to 100% (CH$_3$CN in water) in 40 minutes.

TABLE 2

List of (FITC) Hits

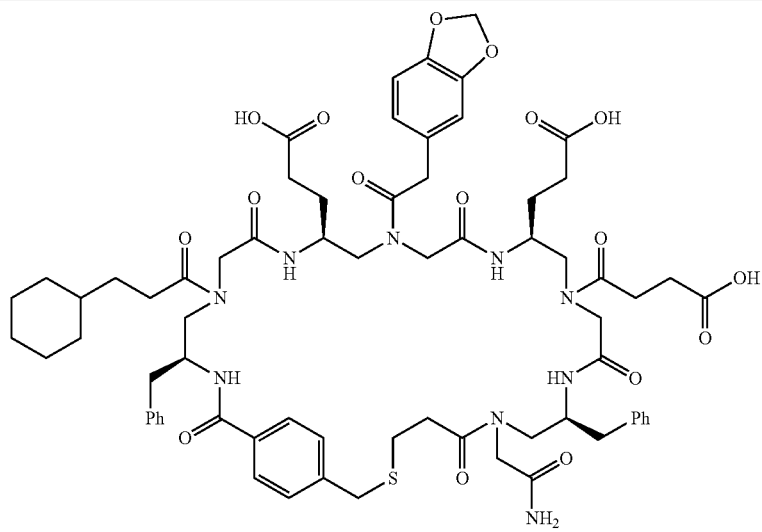 [SMILES: NC(=O)CN1C[C@H](Cc2ccccc2)NC(=O)CN(C(=O)CCC(=O)O)C[C@H](CCC(=O)O)NC(=O)CN(C(=O)Cc2ccc3c(c2)OCO3)C[C@H](CCC(=O)O)NC(=O)CN(C(=O)CCC2CCCCC2)C[C@H](Cc2ccccc2)NC(=O)c2ccc(cc2)CSCCC1=O]

YS-C-84
HRMS (ESI) ([M + H]+)
Calcd. for $C_{69}H_{88}N_9O_{17}S$: 1346.6019
Found: 1346.6050

TABLE 2-continued
List of (FITC) Hits
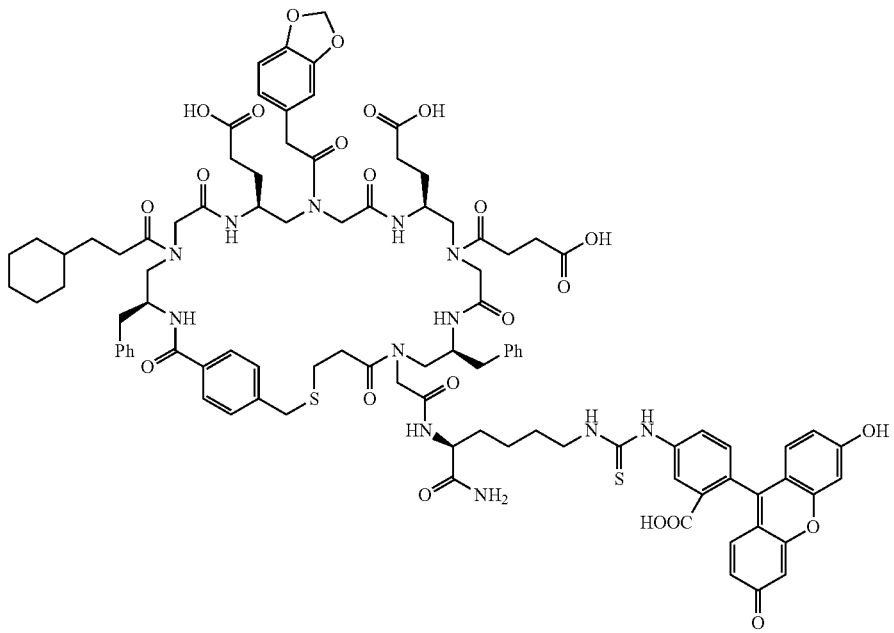 [SMILES: NC(=O)[C@H](CCCCNC(=S)Nc1ccc(-c2c3ccc(=O)cc-3oc3cc(O)ccc23)c(C(=O)O)c1)NC(=O)CN1C[C@H](Cc2ccccc2)NC(=O)CN(C(=O)CCC(=O)O)C[C@H](CCC(=O)O)NC(=O)CN(C(=O)Cc2ccc3c(c2)OCO3)C[C@H](CCC(=O)O)NC(=O)CN(C(=O)CCC2CCCCC2)C[C@H](Cc2ccccc2)NC(=O)c2ccc(cc2)CSCCC1=O]
YS-D-44 (YS-C-84-FITC)
HRMS (ESI) ([M + H]+)
Calcd. for $C_{96}H_{111}N_{12}O_{23}S_2$: 1863.7326
Found: 1863.7375
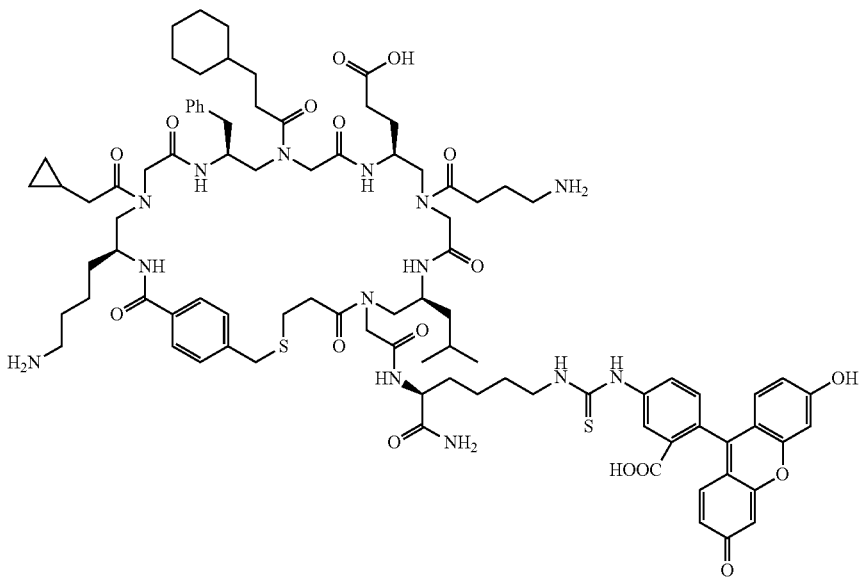 [SMILES: CC(C)C[C@H]1CN(CC(=O)N[C@@H](CCCCNC(=S)Nc2ccc(-c3c4ccc(=O)cc-4oc4cc(O)ccc34)c(C(=O)O)c2)C(N)=O)C(=O)CCSCc2ccc(cc2)C(=O)N[C@@H](CCCCN)CN(C(=O)CC2CC2)CC(=O)N[C@@H](Cc2ccccc2)CN(C(=O)CCC2CCCCC2)CC(=O)N[C@@H](CCC(=O)O)CN(C(=O)CCCN)CC(=O)N1]
YS-D-45
HRMS (ESI) ([M + H]+)
Calcd. for $C_{90}H_{121}N_{14}O_{17}S_2$: 1733.8476
Found: 1733.8505

TABLE 2-continued
List of (FITC) Hits
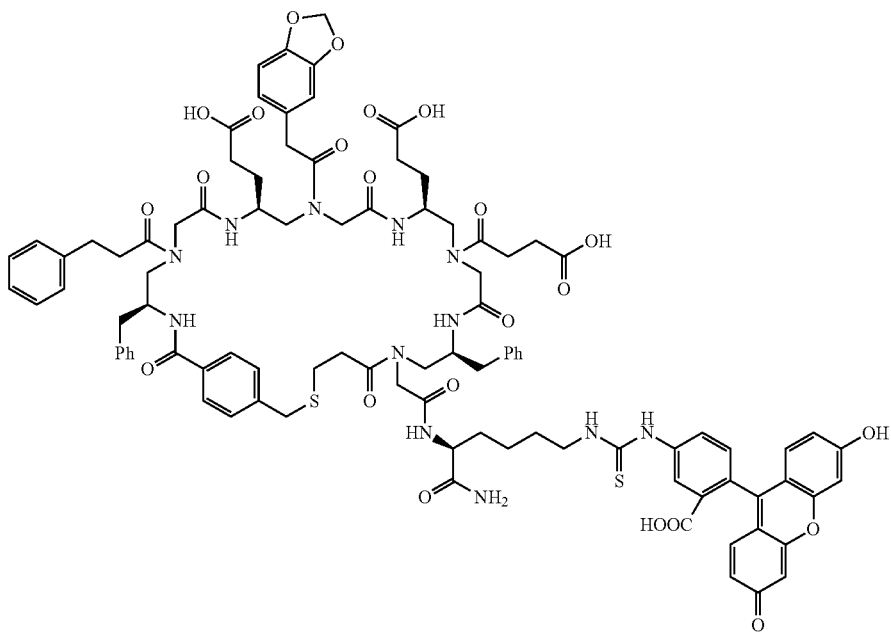 [SMILES: NC(=O)[C@H](CCCCNC(=S)Nc1ccc(-c2c3ccc(=O)cc-3oc3cc(O)ccc23)c(C(=O)O)c1)NC(=O)CN1C[C@H](Cc2ccccc2)NC(=O)CN(C(=O)CCC(=O)O)C[C@H](CCC(=O)O)NC(=O)CN(C(=O)Cc2ccc3c(c2)OCO3)C[C@H](CCC(=O)O)NC(=O)CN(C(=O)CCc2ccccc2)C[C@H](Cc2ccccc2)NC(=O)c2ccc(cc2)CSCCC1=O]
YS-D-65
HRMS (ESI) ([M + H]+)
Calcd. for $C_{96}H_{105}N_{12}O_{23}S_2$: 1857.6857
Found: 1857.6884
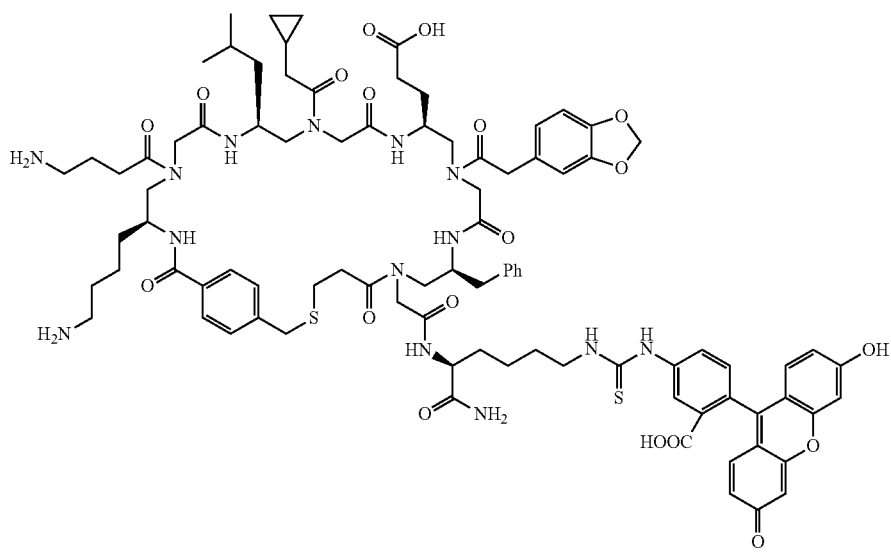 [SMILES: CC(C)C[C@H]1CN(C(=O)CC2CC2)CC(=O)N[C@@H](CCC(=O)O)CN(C(=O)Cc2ccc3c(c2)OCO3)CC(=O)N[C@@H](Cc2ccccc2)CN(CC(=O)N[C@@H](CCCCNC(=S)Nc2ccc(-c3c4ccc(=O)cc-4oc4cc(O)ccc34)c(C(=O)O)c2)C(N)=O)C(=O)CCSCc2ccc(cc2)C(=O)N[C@@H](CCCCN)CN(C(=O)CCCN)CC(=O)N1]
YS-D-51
HRMS (ESI) ([M + H]+)
Calcd. for $C_{90}H_{113}N_{14}O_{19}S_2$: 1757.7748
Found: 1757.7797

TABLE 2-continued
List of (FITC) Hits
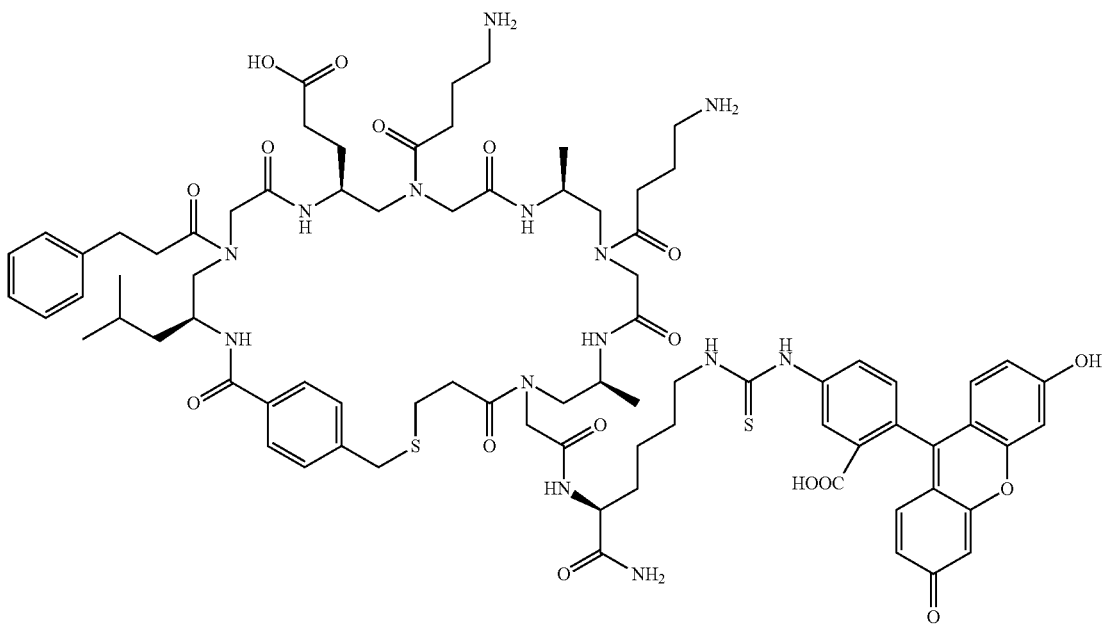 [SMILES: CC(C)C[C@H]1CN(C(=O)CCc2ccccc2)CC(=O)N[C@@H](CCC(=O)O)CN(C(=O)CCCN)CC(=O)N[C@@H](C)CN(C(=O)CCCN)CC(=O)N[C@@H](C)CN(CC(=O)N[C@@H](CCCCNC(=S)Nc2ccc(-c3c4ccc(=O)cc-4oc4cc(O)ccc34)c(C(=O)O)c2)C(N)=O)C(=O)CCSCc2ccc(cc2)C(=O)N1]
YS-D-52
HRMS (ESI) ([M + H]+)
Calcd. for $C_{80}H_{105}N_{14}O_{17}S_2$: 1597.7224
Found: 1597.3252
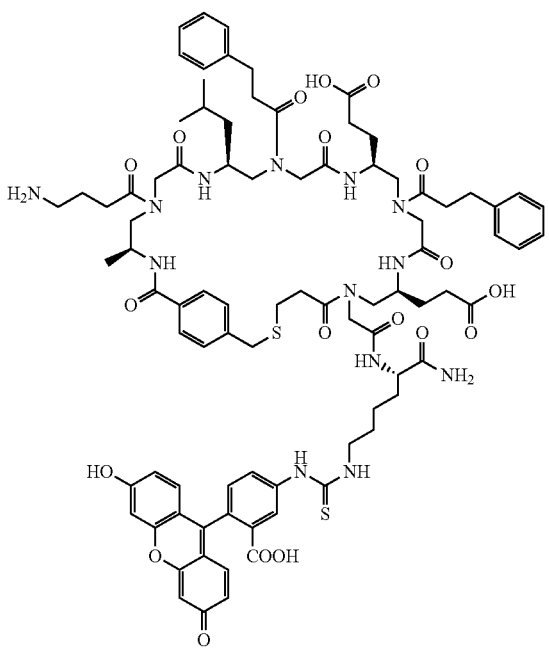 [SMILES: CC(C)C[C@H]1CN(C(=O)CCc2ccccc2)CC(=O)N[C@@H](CCC(=O)O)CN(C(=O)CCc2ccccc2)CC(=O)N[C@@H](CCC(=O)O)CN(CC(=O)N[C@@H](CCCCNC(=S)Nc2ccc(-c3c4ccc(=O)cc-4oc4cc(O)ccc34)c(C(=O)O)c2)C(N)=O)C(=O)CCSCc2ccc(cc2)C(=O)N[C@@H](C)CN(C(=O)CCCN)CC(=O)N1]
YS-D-53
HRMS (ESI) ([M + H]+)
Calcd. for $C_{87}H_{108}N_{13}O_{19}S_2$: 1702.7326
Found: 1702.7371

TABLE 2-continued

List of (FITC) Hits

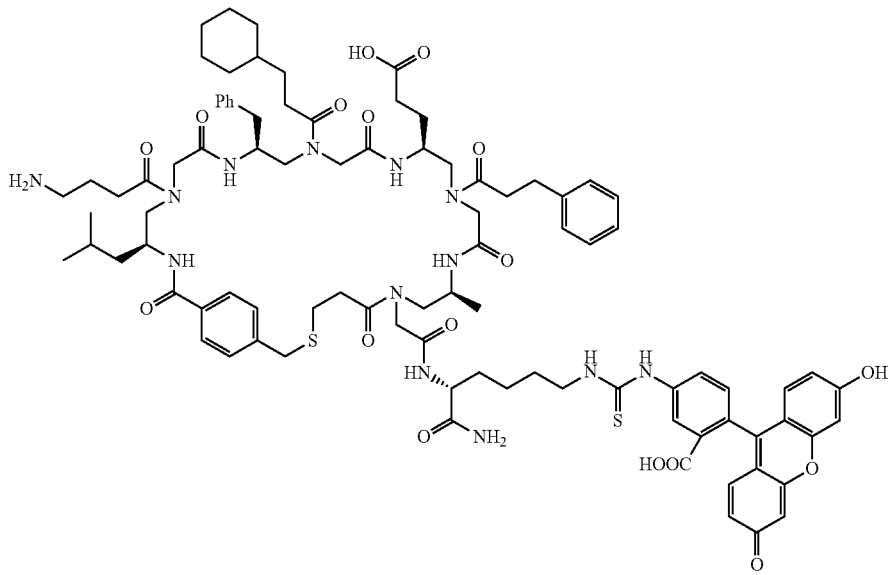 [SMILES: CC(C)C[C@H]1CN(C(=O)CCCN)CC(=O)N[C@@H](Cc2ccccc2)CN(C(=O)CCC2CCCCC2)CC(=O)N[C@@H](CCC(=O)O)CN(C(=O)CCc2ccccc2)CC(=O)N[C@@H](C)CN(CC(=O)N[C@H](CCCCNC(=S)Nc2ccc(-c3c4ccc(=O)cc-4oc4cc(O)ccc34)c(C(=O)O)c2)C(N)=O)C(=O)CCSCc2ccc(cc2)C(=O)N1]

YS-D-54
HRMS (ESI) ([M + H]+)
Calcd. for $C_{91}H_{116}N_{13}O_{17}S_2$: 1726.8054
Found: 1726.8122

Fluorescence Polarization (FP)

Figure 11:
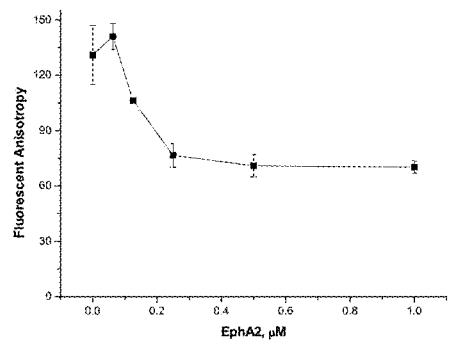
FIG. 11 illustrates the $K_d$ data for the FITC hits.
Figure 11:
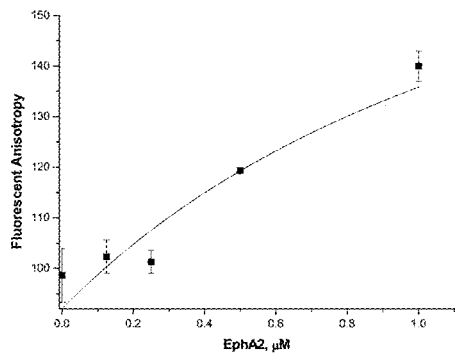
Figure 11:
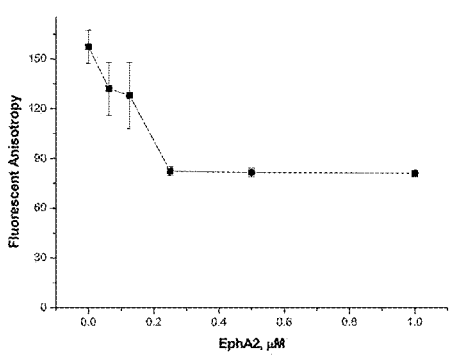
Figure 11:
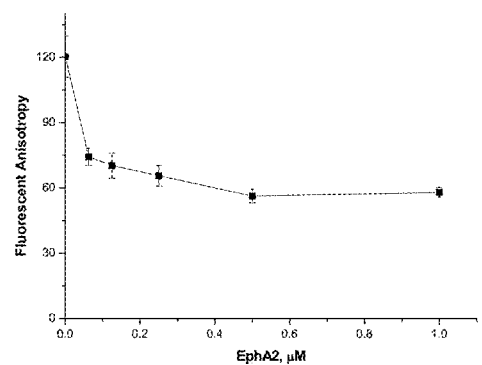
Figure 11:
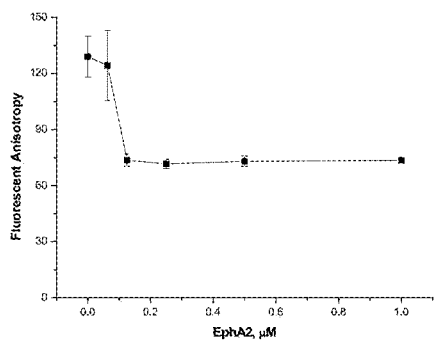

The binding affinity ($K_D$) of the hits was investigated by fluorescence polarization. FP experiment was performed by incubating 50 nM FITC labeled peptide with EphA2 (0.0625 to 2 µM) in 1×PBS. The binding affinity of the lead compound to the GST protein ($K_D$) was obtained by incubating 50 nM FITC labeled AApeptide in GST ranging from 0.3125 to 55 µM. Dissociation constants ($K_D$) were determined by plotting the fluorescence anisotropy values as a function of protein concentration, and the plots were fitted to the following equation (FIG. 11). The $L_{st}$ is the concentration of the peptide and the x stands for the concentration of the protein.

$$Y = [FPmin + (FPmin - FPmin)] \frac{(Kd + L_{st} + x) - \sqrt{(Kd + L_{st} + x)^2 - 4L_{st}x}}{2L_{st}}$$

Bioactivity

In Vitro Kinase Assays and Immunoblotting

In vitro kinase assay to evaluate EphA2 kinase activity was performed as described before. Briefly, 50 µl kinase reaction containing 50 ng recombinant EphA2, 50 µg Poly (Glu-Tyr) and 200 µM ATP and 2 µM of C-84 were incubated at 30° C. for 40 minutes. The reaction was stopped by addition of gel loading buffer. The samples were boiled for 5 minutes and SDS PAGE was performed. Immunoblotting with pTyr-HRP antibody (1:2000 dilution) was performed to detect substrate phosphorylation. The extent of phosphorylation was quantified using ImageJ software. For studying the activity of the compounds in cells, C13 cells were treated at indicated doses for 24 hours. The cells were lysed in lysis buffer and immunoblot analysis was performed.

Migration and Invasion Assays

Invasion and migration assays were performed as described before. Cells were plated into the top chambers and treated with either vehicle or 10 µM C-84. 24 hours later cells in top chamber were scraped and migrated cells were fixed with crystal violet staining.

The foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

The invention claimed is:

1. A method of inhibiting EphA2, comprising administering to a subject in need thereof a therapeutically effective amount of a compound of Formula (I), or a pharmaceutically acceptable salt thereof, (I)

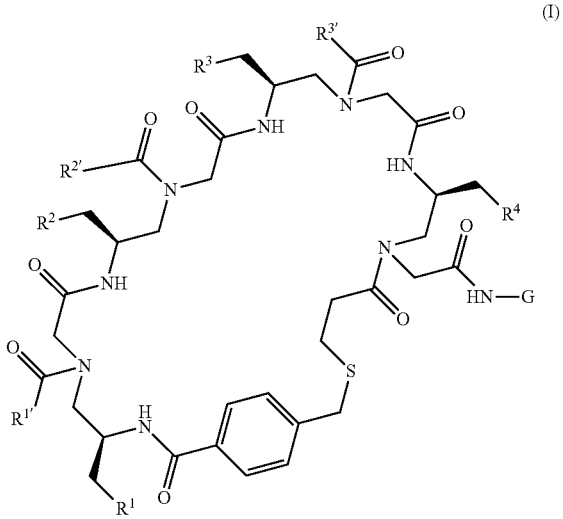

wherein:
R$^1$, R$^2$, R$^3$, R$^4$, R$^{1\prime}$, R$^{2\prime}$, and R$^{3\prime}$ are each independently selected from the group consisting of hydrogen, C$_{1-6}$alkyl, C$_{1-6}$haloalkyl, -L$^1$-G$^1$, -L$^1$-NH$_2$, -L$^1$-NH(C$_{1-4}$alkyl), -L$^1$-N(C$_{1-4}$alkyl)$_2$, -L$^1$-C(O)OH, -L$^1$-C(O)OC$_{1-4}$alkyl, -L$^1$-C(O)NH$_2$, and -L$^1$-C(O)NH(C$_{1-4}$alkyl);
G is H or a solid support, the solid support being optionally substituted with a peptide sequence coding for R$^1$, R$^2$, R$^3$, R$^4$, R$^{1\prime}$, R$^{2\prime}$, and R$^{3\prime}$;
L$^1$ is a bond or a C$_{1-4}$alkylene; and
G$^1$ is C$_{3-8}$cycloalkyl, aryl, a 4- to 12-membered heterocyclyl, or a 5- to 12-membered heteroaryl, wherein G$^1$ is optionally substituted with 1-4 substituents independently selected from the group consisting of C$_{1-4}$alkyl, C$_{1-4}$haloalkyl, and halogen, or a pharmaceutically acceptable salt thereof, or a pharmaceutical composition comprising a compound of Formula (I), or a pharmaceutically acceptable salt thereof, and a pharmaceutically acceptable carrier.

2. The method of claim 1, wherein the compound is

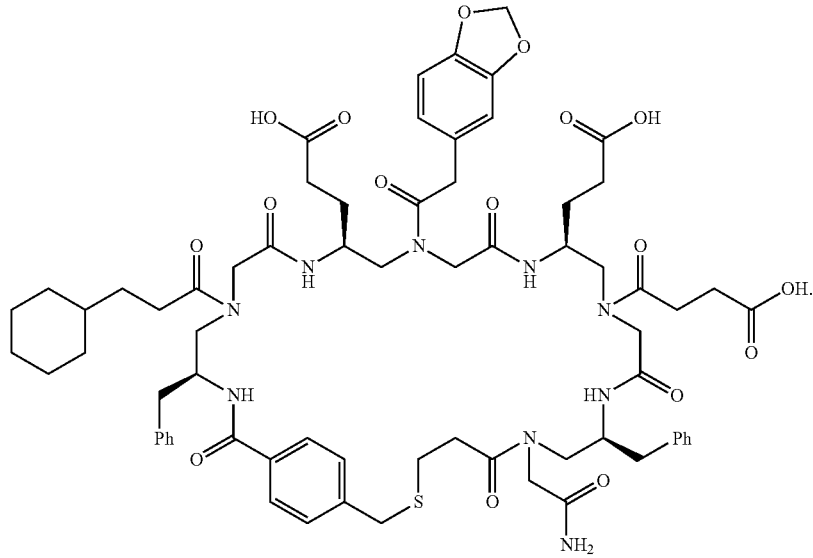 [SMILES: NC(=O)CN1C[C@H](Cc2ccccc2)NC(=O)CN(C(=O)CCC(=O)O)C[C@H](CCC(=O)O)NC(=O)CN(C(=O)Cc2ccc3c(c2)OCO3)C[C@H](CCC(=O)O)NC(=O)CN(C(=O)CCC2CCCCC2)C[C@H](Cc2ccccc2)NC(=O)c2ccc(cc2)CSCCC1=O]

or a pharmaceutically acceptable salt thereof.

3. The method of claim 1, wherein:
R$^1$, R$^2$, R$^3$, R$^4$, R$^{1\prime}$, R$^{2\prime}$, and R$^{3\prime}$ are each independently selected from the group consisting of hydrogen, C$_{1-6}$alkyl, -L$^1$-G$^1$, —C$_{1-4}$alkylene-NH$_2$, —C$_{1-4}$alkylene-NH(C$_{1-4}$alkyl), —C$_{1-4}$alkylene-N(C$_{1-4}$alkyl)$_2$, —C$_{1-4}$alkylene-C(O)OH, —C$_{1-4}$alkylene-C(O)OC$_{1-4}$alkyl, —C$_{1-4}$alkylene-C(O)NH$_2$, and —C$_{1-4}$alkylene-C(O)NH(C$_{1-4}$alkyl).

4. The method of claim 1, wherein:
G$^1$ is C$_{3-8}$cycloalkyl, phenyl, or a 4- to 12-membered heterocyclyl, wherein G$^1$ is optionally substituted with 1-4 substituents independently selected from the group consisting of C$_{1-4}$alkyl, C$_{1-4}$haloalkyl, and halogen.

5. The method of claim 1, wherein:
R$^1$ is hydrogen, aryl, C$_{1-6}$alkyl, or —C$_{1-4}$alkylene-NH$_2$;
R$^{1\prime}$ is —C$_{1-4}$alkylene-NH$_2$ or —C$_{1-4}$alkylene-G$^1$, where G$^1$ is C$_{3-8}$cycloalkyl or aryl;
R$^2$ is —C$_{1-4}$alkylene-C(O)OH, aryl, or C$_{1-6}$alkyl;
R$^{2\prime}$ is —C$_{1-4}$alkylene-NH$_2$ or —C$_{1-4}$alkylene-G$^1$, where G$^1$ is C$_{3-8}$cycloalkyl, aryl, or a 4- to 12-membered heterocyclyl;
R$^3$ is hydrogen or —C$_{1-4}$alkylene-C(O)OH;
R$^{3\prime}$ is —C$_{1-4}$alkylene-NH$_2$, —C$_{1-4}$alkylene-C(O)OH, or —C$_{1-4}$alkylene-G$^1$, where G$^1$ is aryl or a 4- to 12-membered heterocyclyl; and
R$^4$ is hydrogen, C$_{1-6}$alkyl, —C$_{1-4}$alkylene-C(O)OH, or aryl.

6. The method of claim 1, wherein:
R$^1$ is aryl;
R$^{1\prime}$ is —C$_{1-4}$alkylene-C$_{3-8}$cycloalkyl;
R$^2$ is —C$_{1-4}$alkylene-C(O)OH;
R$^{2\prime}$ is —C$_{1-4}$alkylene-G$^1$, where G$^1$ is a 4- to 12-membered heterocyclyl;
R$^3$ is —C$_{1-4}$alkylene-C(O)OH;
R$^{3\prime}$ is —C$_{1-4}$alkylene-C(O)OH; and
R$^4$ is aryl.

7. The method of claim 1, wherein G is hydrogen.

8. The method of claim 1, wherein G is a solid support, wherein the solid support comprises a peptide sequence coding for R$^1$, R$^2$, R$^3$, R$^4$, R$^{1\prime}$, R$^{2\prime}$, and R$^{3\prime}$.

9. The method of claim 8, wherein the solid support further comprises an interior portion and an exterior portion, wherein the peptide sequence is attached to the interior portion and the macrocyclic peptidomimetic portion of formula (I)

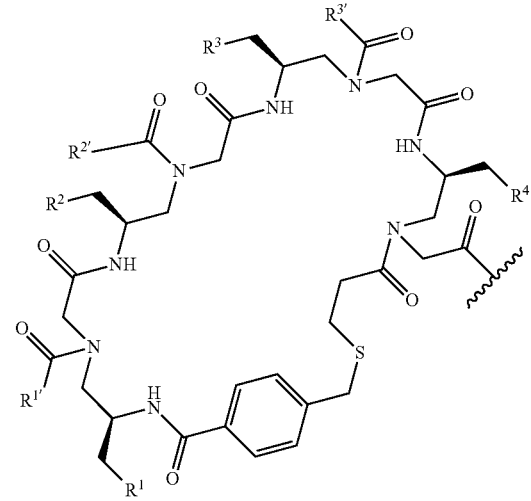

is attached to the exterior portion.

10. The method of claim 9, wherein the peptide sequence and the macrocyclic peptidomimetic portion of formula (I) are independently attached to amino groups located, respectively, on the interior portion and the exterior portion.

11. The method of claim 1, wherein inhibiting EphA2 comprises reducing EphA2 overexpression.

12. The method of claim 1, wherein inhibiting EphA2 comprises reducing EphA2-mediated cell signaling.

\* \* \* \* \*